US006403782B1

(12) United States Patent
Luster et al.

(10) Patent No.: US 6,403,782 B1
(45) Date of Patent: Jun. 11, 2002

(54) NUCLEIC ACID ENCODING EOTAXIN

(75) Inventors: Andrew D. Luster, Wellesley; Philip Leder, Chestnut Hill; Marc Rothenberg, Brookline; Eduardo Garcia, Somerville, all of MA (US)

(73) Assignees: President and Fellows of Harvard College, Cambridge; The General Hospital Corporation, Boston, both of MA (US)

( * ) Notice: Subject to any disclaimer, the term of this patent is extended or adjusted under 35 U.S.C. 154(b) by 0 days.

(21) Appl. No.: 09/366,887

(22) Filed: Aug. 4, 1999

Related U.S. Application Data

(63) Continuation of application No. 08/522,713, filed on Sep. 1, 1995, now abandoned.
(60) Provisional application No. 60/000,449, filed on Jun. 22, 1995.

(51) Int. Cl.$^7$ .......................... C12N 15/19; C12N 15/63
(52) U.S. Cl. .................. 536/23.5; 530/324; 435/69.5; 435/71.1; 435/71.2; 435/320.1; 435/471; 435/325; 435/252.3; 435/254.11
(58) Field of Search .............................. 536/23.1, 23.5, 536/24.3, 24.31; 435/69.5, 71.1, 71.2, 471, 252.3, 325, 365, 254.11, 320.1; 503/324

(56) References Cited

FOREIGN PATENT DOCUMENTS

WO    WO 9507985    3/1995

OTHER PUBLICATIONS

Mikayama et al. Proc. Natl. Acad. Sci. USA vol. 90, pp. 10056–10060, 1993.*
Voet et al. Biochemistry. John Wiley & Sons, Inc. pp. 126–128 and 228–234, 1993.*
Alam et al., J. Immun. 150:3442 (1993).
Cunningham et al., Science 244:1081–1085 (1989).
Dahinden et al., J. Exp. Med. 179:751 (1994).
George et al., "Macromolecular Sequencing and Synthesis Selected Methods and Applications" pp. 127–149 Alan R. Liss, Inc. N.Y. (1988).
Jose et al., Biochem. & Biophy. Res. Comm. 205(1):788–794 (1994).
Murphy, P., "The molecular biology of leukocyte chemoattractant receptors," Annu. Rev. Immunol. 12:593 (1994).
Ponalli et al., J. of Clinical Investigation 97(3):604–612 (1996).
Rot et al., J. Exp. Med. 176:1489 (1992);.
Springer, T., "Traffic signals for lymphocyte recirculation and leukocyte emigration: The multistep paradigm," Cell 76:301 (1994).
Warringa et al., J. All. Clin. Immun. 91:1198 (1993).
Weber et al., J. Immun. 154:4166 (1995).

* cited by examiner

*Primary Examiner*—Prema Mertz
(74) *Attorney, Agent, or Firm*—Clark & Elbing LLP; Kristina Bieker-Brady, Ph.D.

(57) ABSTRACT

Disclosed is substantially pure eotaxin DNA sequence and eotaxin polypeptide, and methods of using such DNA and polypeptide to direct chemotaxis of eosinophils. Methods are provided for the treatment diseases and disorders such as inflammation and tumorigenesis.

11 Claims, 18 Drawing Sheets

FIG. 3A

```
CCCGGCCAGTAACTTCCATCTGTCTCCCTCCACCATGCAGAGCTCCACAGCGCTTCTATT
                                 M  Q  S  S  T  A  L  L  F                60

CCTGCTGCTCACGGTCACTTCCTTCACCTCCCAGGTGCTGGCTCACCCAGGCTCCATCCC
 L  L  L  T  V  T  S  F  T  S  Q  V  L  A  H  P  G  S  I  P            120
                                              ↑

AACTTCCTGCTGCTTTATCATGACCAGTAAGAAGATCCCCAACACACTACTGAAGAGCTA
 T  S  C  C  F  I  M  T  S  K  K  I  P  N  T  L  L  K  S  Y            180

CAAAAGAATCACCAACAACAGATGCACCCTGAAAGCCATAGTCTTCAAGACCAGGTTCGG
 K  R  I  T  N  N  R  C  T  L  K  A  I  V  F  K  T  R  L  G            240

CAAAGAGATCTGTGCTGACCCCAAGAAGAAGTGGGTCCAGCATGCCACAAAGCACCTGGA
 K  E  I  C  A  D  P  K  K  K  W  V  Q  Q  A  T  K  H  L  D            300

CCAAAAACTCCAAACTCCAAAACCATAAACAACCTCCTCTCTTGACACTAACCCAGAGCC
 Q  K  L  Q  T  P  K  P                                                360

TAAGAACTGCTTGATTCCTTCTCTTTCCTAAGACGTGCTCTGACGGAATATCAGCACCAG
                                                                        420
TCGCCCAAGGACTTGGCTTCATGTAGTTCCAGATGGGACTGGAAGTCATTATGTTTCCTG
                                                                        480
AAATAAGTCAGACTCAAAAGATTGTGTAATTTCTTGCATATGCAACATCTTAAAAGGGGG
                                                                        540
GCATGAAAGGAGATGTGGGATTATTGAGGAACACAATGGGACGAGTTAGGAGTAACTGAC
                                                                        600
GATAATAGCAGCTTATACACATATATGAAAATGTCTATTGTTTTGCACAATTAATATACA
                                                                        660
CTAATTAAAATTAATTTACACTAACTAAAATGTTAATATTTAAAGACATGTTACATTTAA
                                                                        720
GAAATTGGAGTTTTAAAGCATAATTTAATGGATATCAGTCCTTTTTGTTATTGTGTTGTT
                                                                        780
TGTTTGCTTGCTTGTTTGAAACAGGGACTCACTGTATCACCCTGACTGACCTGTAACTCA
                                                                        840
CTGTGTAGACCAGGCTGACCTCAAACTCACAGAAATTTACCTGCCTCTGCCTTTAAAGTG
                                                                        900
CTACCATGCCAAGCCAGAATGTTTTTTATTAGAATATACCAATTATATAT AATAA ATAT
                                                                        960
TTTACTACAAAAAAAAAAAAAAAAAAAAAAAAA
                                   → 994
```

FIG. 3B

|     |      |   |   |   |   |   |   |   |   | 10 |   |   |   |   |   |   |   |   |   | 20 |   |
|-----|------|---|---|---|---|---|---|---|---|----|---|---|---|---|---|---|---|---|---|----|---|
| Mu  | Eot  | M | - | - | - | - | - | - | - | -  | - | Q | S | T | A | L | L | F | L | L  | T | V | T |
| Gp  | Eot  | M | - | - | - | - | - | - | - | -  | - | K | V | T | A | F | L | C | L | L  | T | V | S |
| Gp  | MCP1 | M | - | - | - | - | - | - | - | -  | - | Q | R | S | V | L | L | C | L | L  | V | I | E | A |
| Hu  | MCP1 | M | - | - | - | - | - | - | - | -  | - | K | V | S | A | L | L | C | L | L  | L | I | A | A |
| Mu  | MCP1 | M | - | - | - | - | - | - | - | -  | - | Q | V | P | V | M | L | L | G | L  | L | F | T | V | A |
| Hu  | MCP2 | - | - | - | - | - | - | - | - | -  | - | - | - | - | - | - | - | - | - | -  | - | - | - |
| Hu  | MCP3 | M | W | K | P | M | P | S | P | S  | N | M | K | A | S | A | A | L | L | C  | L | L | L | T | A | A |
| Mu  | MCP3 | M | - | - | - | - | - | - | - | -  | - | R | I | S | A | T | L | L | C | L  | L | L | I | A A |

|     |      |   |   |   | 30 |   |   |   |   | ↓ |   |   |   | ** |   |   |   |   |   | 50 |   |
|-----|------|---|---|---|----|---|---|---|---|---|---|---|---|----|---|---|---|---|---|----|---|
| Mu  | Eot  | S | F | T | S  | Q | V | L | A | H | P | G | S | I  | - | - | P | T | S | C  | C | F | I | M | T | S |
| Gp  | Eot  | A | F | S | A  | Q | V | L | A | H | P | G | - | I  | - | - | P | S | A | C  | C | F | R | V | T | N |
| Gp  | MCP1 | T | F | C | S  | L | L | M | A | Q | P | D | G | V  | N | T | P | - | T | C  | C | Y | - | T | F | N |
| Hu  | MCP1 | T | F | I | P  | Q | G | L | A | Q | P | D | A | I  | N | A | P | V | T | C  | C | Y | N | F | T | N |
| Mu  | MCP1 | G | W | S | I  | H | V | L | A | Q | P | D | A | V  | N | A | P | L | T | C  | C | Y | S | F | T | S |
| Hu  | MCP2 | - | - | - | -  | - | - | - | A | Q | P | D | S | V  | S | I | P | I | T | C  | C | F | N | V | I | N |
| Hu  | MCP3 | A | F | S | P  | Q | G | L | A | Q | P | V | G | I  | N | T | S | T | C | C  | Y | R | F | I | N |
| Mu  | MCP3 | A | F | S | T  | Q | V | W | A | Q | P | D | G | P  | N | A | S | - | T | C  | C | Y | - | V | K | K |

|     |      |   |   |   |   |   |   | 60 |   |   |   |   |   |   |   | 70 |   |   |   |   |   |
|-----|------|---|---|---|---|---|---|----|---|---|---|---|---|---|---|----|---|---|---|---|---|
| Mu  | Eot  | K | K | I | P | N | Y | L  | L | K | S | Y | K | R | I | T  | N | N | R | C | L | K | A | I | V |
| Gp  | Eot  | K | K | I | S | F | Q | R  | L | K | S | Y | K | I | I | T  | S | S | K | C | P | Q | T | A | I | V |
| Gp  | MCP1 | K | Q | I | P | L | K | R  | V | K | G | Y | E | R | I | T  | S | S | R | C | P | Q | E | A | V | I |
| Hu  | MCP1 | R | K | I | S | V | Q | R  | L | A | S | Y | R | R | I | T  | S | S | K | C | P | K | E | A | V | I |
| Mu  | MCP1 | K | M | I | P | M | S | R  | L | E | S | Y | K | R | I | T  | S | S | R | C | P | K | E | A | V | V |
| Hu  | MCP2 | R | K | I | P | I | Q | R  | L | E | S | Y | T | R | I | T  | N | I | Q | C | P | K | E | A | V | I |
| Hu  | MCP3 | K | K | I | P | K | Q | R  | L | E | S | Y | R | R | T | T  | S | S | H | C | P | R | E | A | V | I |
| Mu  | MCP3 | Q | K | I | P | K | R | N  | L | K | S | Y | R | R | I | T  | S | S | R | C | P | W | E | A | V | I |

|     |      |   |   |   | 80 |   |   |   |   |   |   |   |   | +++ |   |   |   |   | 100 |   |
|-----|------|---|---|---|----|---|---|---|---|---|---|---|---|-----|---|---|---|---|-----|---|
| Mu  | Eot  | F | K | T | R  | L | G | K | E | I | C | A | D | P   | K | K | K | W | V   | Q | D | A | T | K | H | L |
| Gp  | Eot  | F | E | I | K  | P | D | K | M | I | C | A | D | P   | K | K | W | V | Q   | D | A | K | Y |
| Gp  | MCP1 | F | R | T | L  | K | N | E | V | C | A | D | P | T   | Q | K | W | V | Q   | D | Y | I | A | K | L |
| Hu  | MCP1 | F | K | T | I  | V | A | K | E | I | C | A | D | P   | K | Q | K | W | V   | Q | D | S | M | D | H |
| Mu  | MCP1 | F | V | T | K  | L | K | R | E | V | C | A | D | P   | K | K | E | W | V   | Q | T | Y | I | K | N |
| Hu  | MCP2 | F | K | T | K  | R | G | K | E | V | C | A | D | P   | K | E | R | W | V   | R | D | S | M | K | H | L |
| Hu  | MCP3 | F | K | T | K  | L | D | K | E | I | C | A | D | P   | T | Q | K | W | V   | Q | D | F | M | K | H | L |
| Mu  | MCP3 | F | K | T | K  | K | G | M | E | V | C | R | E | A   | H | Q | K | W | V   | E | E | A | I | A | Y | L |

|     |      |   |   |   | 110 |   |   |   |   |   |
|-----|------|---|---|---|-----|---|---|---|---|---|
| Mu  | Eot  | D | Q | K | L   | Q | T | P | K | P |
| Gp  | Eot  | D | Q | I | S   | Q | T | T | K | P |
| Gp  | MCP1 | D | Q | R | T   | Q | K | Q | N |
| Hu  | MCP1 | D | K | Q | T   | Q | T | P | K | T |
| Mu  | MCP1 | D | R | N | Q   | M | R | S | E | P |
| Hu  | MCP2 | D | Q | I | F   | Q | N | L | K | P |
| Hu  | MCP3 | D | K | K | T   | Q | T | P | K | L |
| Hu  | MCP3 | D | M | K | T |

FIG. 7

```
CTCGTCCCGCTCGTGCCCTGCGAACAACCCAGAAACTATTGTCACGCTGCAACCTGCACACTGAAAGTCTCCACACGGTTCTGTCTGCCTGCT
                                        M  K  V  S  T  A  F  L  C  L  L
                                                                                                100

GCTCACAGTCTGCTTTCAGGGCCCAGGTGCTCGCCCATCCAGGTATCCCAAGTGCTGCTTCCGTGTGACCAATAAGAAGATCTCCTTTCAGCCA
 L  T  V  S  A  F  S  A  Q  V  L  ◀  H  P  G  I  P  S  A  C  C  F  R  V  T  N  K  K  I  S  F  Q  R
                                                                                                200

CTGAAGAGCTACAAAATAATCACCAGCAGCAAATGCCCCAGAGACAGCCATTGTGTCTTTGAGATCAAACCTGACAAATGTATGTGCCGACCCAAGAAGA
 L  K  S  Y  K  I  I  T  S  S  K  C  P  Q  T  A  I  V  F  E  I  K  P  D  K  H  I  C  A  D  P  K
                                                                                                300

AGTGGGTTCAGGATGCCAAGAAGTACCTGGACCAAATATCCAAACTACAAAGCCGTAATCATCGTGCTTGAGATGACAAACCAGAAATTGCTTGATTT
 K  V  V  Q  D  A  K  K  Y  L  D  Q  I  S  Q  T  T  K  P
                                                                                                400

ATTTTTCCTTCTAAAATGCATTCTGAAATATAATATTATTCCCAAAGGGATGACTTTTATTTAATAATTTTAAAAAGCAAATGCATTTAAGTTATC
                                                                                                500

AGTCTCTTAAACATATCTTTATGTATATCACTCATTTTTAAAGGTTGCCTTGCTCTCTGAACTCCCATCCGGTGACTCCTACCCTCCCATGTGTAGGAAATGTCA
                                                                                                600

CTCCAGGCTTGCCTGGAGACTCTCTTTCTCCTACCCTCGTAAGGATCCAACAAGACCATTGATGTGAAATGCCTTTAATTTTTCAGAGGAC
                                                                                                700

ATTGTCTTGTGAAGCCAGGTTGTGATTCACAGTGAGTGGAAGTAAATGTGTTTCAGAATACATGAAATATATACACTTTATTACTGCTAAAA
                                                                                                800

AAAAAAAAAAAAAAAA
               ────▶ 818
```

FIG. 12A

HUMAN EOTAXIN

EXON 1

CGA GCG GCC GCC CGG GCG AGG TCA ACC CAG AAA CCA CCA CCT CTC ACG CCA AAG

CTC ACA CCT TCA GCC TCC AAC ATG AAG GTC TCC GCA GCA CTT CTG TGG CTG CTG
                                        M   K   V   S   A   A   L   L   W   L   L

CTC ATA GCA GCT GCC TTC AGC CCC CAG GGG CTC GCT GGG CCAG
 L   I   A   A   A   F   S   P   Q   G   L   A↑G   P

↑ Signal peptidase cleavage

FIG. 12B

HUMAN EOTAXIN

EXON 2

TTT TTT TTC TTC CTG TTC ATT TTT CCC CAA AAT TCA GCT TCT GTC CCA ACC
                                              A   S   V   P   T

ACC TGC TGC TTT AAC CTG GCC AAT AGG AAG ATA CCC CTT CAG CGA CTA GAG AGC
 T   C   C   F   N   L   A   N   R   K   I   P   L   Q   R   L   E   S

TAC AGG AGA ATC ACC AGT GGC AAA TGT CCC CAG AAA GCT GTG ATG
 Y   R   R   I   T   S   G   K   C   P   Q   K   A   V   I

Underlining indicates splice acceptor site or splice donor site

FIG. 12C

HUMAN EOTAXIN

EXON 3

ATC TCC CAC AGC TTC AAG ACC AAA CTG GCC AAG GAT ATC TGT GCC GAC CCC AAG
 I   S   H   S   F   K   T   K   L   A   K   D   I   C   A   D   P   K

AAG AAG TGG GTG CAG GAT TCC ATG AAG TAT CTG GAC CAA AAA TCT CCA ACT CCA
 K   K   W   V   Q   D   S   M   K   Y   L   D   Q   K   S   P   T   P

AAG CCA TAA ATA ATC ACC ATT TTT GAA ACC AAA CCA GAG CCT GAG TGT TGC CTA
 K   P   *

ATT TGT TTT CCC TTC TTA CAA TGC ATT CTG AGG TAA CCT CAT TAT CAG TCC AAA

GGG CAT GGG TTT TAT TAT ATA TAT TTT TTT TAA AAA AAA ACG TAT

TGC ATT TAA TTT ATT GAG GCT TTA AAA CTT ATG ATC CTC CAT GAA TAT CAG TTA

TTT TTA AAC TGT AAA GCT ATC GAT ACC GT

FIG. 13

HPG IPSACCFRVTNKKIISFQRLKSYKIITSSKCPQTAIVFEIKPDKMICADPKKKWVQDAKKYLDQISQTTKP  G.PIG
HPGSIPTSCCFIMTSKKIPNTLLKSYKRITNNRCTLKAIVFKTRLGKEICADPKKKWVQDATKHLDQKLQTPKP  MURINE
GPASVPTTCCFNLANRKIPLQRLESYRRITSGKCPQKAVIFKTKLAKDICADPKKKWVQDSMKYLDQKSPTPKP  HUMAN

Expression of eotaxin in ulcerative colitis lesions

Total RNA was extracted from resected colons of ulcerative colitis patients (lanes 3-7) and normal colons (lanes 1-2), fractionated on a 1.2% agarose/formaldehyde gel, transferred to GeneScreen and hybdidized with a human eotaxin probe.

NUCLEIC ACID ENCODING EOTAXIN

CROSS REFERENCE TO RELATED APPLICATION

This application is a Continuation application of U.S. patent application Ser. No. 08/522,713 filed Sep. 1, 1995 now abandoned which is related to the provisional application filed Jun. 22, 1995 having serial No. 60/000,449, both of which the entire contents are incorporated herein by reference.

STATEMENT AS TO FEDERALLY SPONSORED RESEARCH

This work was funded in part by NIH grant DK43351. The Federal Government has certain rights to the invention.

FIELD OF THE INVENTION

The invention relates to regulation of the immune system.

BACKGROUND OF THE INVENTION

The chemokines are a family of 8–12 kD proteins that regulate leukocyte trafficking by binding to specific seven transmembrane spanning G-protein-linked receptors. They can be divided into three families depending upon the sequence of conserved cysteine residues and this structural distinction corresponds to specific biologic properties in that the C-X-C, C-C, and C families are mainly chemoattractive for neutrophils, monocytes, and lymphocytes, respectively. Additionally, each chemokine family maps to a different chromosomal locus.

Eosinophils are circulating leukocytes that survive for several weeks. They dwell predominantly in tissues where they mediate pro-inflammatory and cytotoxic damage in selected diseases (e.g. asthma, parasitic infections, and malignancy). Given their presumed role in the pathogenesis of inflammatory states, the regulation of tissue recruitment of eosinophils is of interest and various chemoattractants have been found to be active on eosinophils, including leukotriene B4, platelet activating factor (PAF), and several chemokines (Resnick, et al. (1993) Amer. J. Resp. Cell. Mol. Biol. 8, 349–355). Chemokines active on eosinophils include certain C-C chemokines: monocyte chemoattractive protein (MCP)-2 and 3, RANTES, and macrophage inflammatory protein (MIP)-1a (Rot, et al. (1992) J. Exp. Med 176, 1489–1495; Alam, R. et al. (1993) J. Immun. 150, 3442–3448; Dahinden, et al. (1994) J. Exp. Med. 179, 751–756; Weber, et al. (1995) J. Immun. 154, 4166–4172). A C-X-C chemokine, interleukin-8 (IL-8), is also chemoattractive for cytokine-primed eosinophils (Warringa et al. (1993) J. All. Clin. Immun. 91, 1198–1205). Notwithstanding their activity, none of these chemoattractive molecules are eosinophil specific and their relative importance in selected diseases and in experimental animal models of allergy remains unclear.

SUMMARY OF THE INVENTION

In general, the invention features substantially pure nucleic acid (for example, genomic DNA, cDNA, or synthetic DNA, or mRNA) encoding an eotaxin polypeptide as defined below. In related aspects, the invention also features a vector, a cell (e.g., a bacterial, yeast, nematode, or mammalian cell), a transgenic animal which includes such a substantially pure DNA encoding an eotaxin polypeptide of the invention or a knockout mutation in the eotaxin gene, and methods for modulating eosinophil chemotaxis.

In preferred embodiments, the eotaxin gene is the human eotaxin gene provided in FIG. 12, the murine eotaxin gene provided in FIG. 3A or the guinea pig eotaxin gene provided in FIG. 7. In various preferred embodiments, the cell is a transformed animal cell such as a human cell or a rodent cell.

In related aspects, the invention features a transgenic animal containing a transgene which encodes an eotaxin polypeptide and use of the eotaxin nucleotide sequence to engineer a transgenic animal having a knockout mutation in the eotaxin gene. The invention also features a cell that expresses the eotaxin gene. Preferably, the cell is an animal cell which is an epithelial or endothelial cell.

In a second aspect, the invention features a substantially pure DNA which includes a promoter capable of expressing the eotaxin gene in a cell. In preferred embodiments, the promoter is the promoter native to an eotaxin gene. Additionally, transcriptional and translational regulatory regions are preferably native to an eotaxin gene. A constitutive promotor or an inducible promotor are also included in the invention.

In other aspects, the invention features a substantially pure oligonucleotide including one or a combination of the sequences shown in FIGS. 3A (SEQ ID NO:5), 7(SEQ ID NO:15), 12A (SEQ ID NO:17), 12B (SEQ ID NO:19), and 12C (SEQ ID NO:21).

In a another aspect, the invention features a method of isolating an eotaxin gene or fragment thereof from a cell, involving: (a) providing a sample of cellular DNA; (b) providing a pair of oligonucleotides having sequence homology to a conserved region of an eotaxin gene (for example, oligonucleotides which include fragments of the sequences shown in FIGS. 3A (SEQ ID NO:5), 7 (SEQ ID NO:15), 12A (SEQ ID NO:17), 12B (SEQ ID NO:19), and 12C (SEQ ID NO:21) which are conserved as evidenced by the homologies shown in FIG. 3B (SEQ ID NOS.7–14(c) combining the pair of oligonucleotides with the cellular DNA sample under conditions suitable for polymerase chain reaction-mediated DNA amplification; and (d) isolating the amplified eotaxin gene or fragment thereof. Where a fragment is obtained by PCR, standard library screening techniques may be used to obtain the complete coding sequence.

In preferred embodiments, amplification is carried out using a reverse-transcription polymerase chain reaction, for example, the RACE method.

In another aspect, the invention features a method of identifying a eotaxin gene in a cell, involving: (a) providing a preparation of cellular DNA (for example, from the human genome); (b) providing a detectably-labelled DNA sequence (for example, prepared by the methods of the invention) having homology to a conserved region of an eotaxin gene; (c) contacting the preparation of cellular DNA with the detectably-labelled DNA sequence under hybridization conditions providing detection of genes having 50% or greater sequence identity; and (d) identifying an eotaxin gene by its association with the detectable label.

In another aspect, the invention features a method of isolating an eotaxin gene from a recombinant DNA library, involving: (a) providing a recombinant DNA library; (b) contacting the recombinant DNA library with a detectably-labelled gene fragment produced according to the PCR method of the invention under hybridization conditions providing detection of genes having 50% or greater sequence identity; and (c) isolating an eotaxin gene by its association with the detectable label.

In another aspect, the invention features a method of isolating an eotaxin gene from a recombinant DNA library, involving: (a) providing a recombinant DNA library; (b) contacting the recombinant DNA library with a detectably-labelled Eotaxin oligonucleotide of the invention under hybridization conditions providing detection of genes having 50% or greater sequence identity; and (c) isolating an eotaxin gene by its association with the detectable label.

In another aspect, the invention features an eotaxin gene isolated according to the method involving: (a) providing a sample of cellular DNA; (b) providing a pair of oligonucleotides having sequence homology to a conserved region of an eotaxin gene; (c) combining the pair of oligonucleotides with the cellular DNA sample under conditions suitable for polymerase chain reaction-mediated DNA amplification; and (d) isolating the amplified eotaxin gene or fragment thereof.

In another aspect, the invention features an eotaxin gene isolated according to the method involving: (a) providing a preparation of cellular DNA; (b) providing a detectably-labelled DNA sequence having homology to a conserved region of an eotaxin gene; (c) contacting the preparation of DNA with the detectably-labelled DNA sequence under hybridization conditions providing detection of genes having 50% or greater sequence identity; and (d) identifying an eotaxin gene by its association with the detectable label.

In another aspect, the invention features an eotaxin gene isolated according to the method involving: (a) providing a recombinant DNA library; (b) contacting the recombinant DNA library with a detectably-labelled eotaxin gene fragment produced according to the method of the invention under hybridization conditions providing detection of genes having 50% or greater sequence identity; and (c) isolating an eotaxin gene by its association with the detectable label.

In another aspect, the invention features a method of identifying an eotaxin gene involving: (a) providing a mammalian cell sample; (b) introducing by transformation (e.g. viral, chemical, or mechanical transformation) into the cell sample a candidate eotaxin gene; (c) expressing the candidate eotaxin gene within the cell sample or isolating eotaxin from the tissue sample or protein isolated therefrom; and (d) determining whether the cell sample elicits an alteration in eosinophil chemotaxis, whereby an increased eosinophil specific chemotactic increase identifies an eotaxin gene.

In another aspect, the invention features an eotaxin gene isolated according to the method involving: (a) providing a cell sample; (b) introducing by transformation into the cell sample a candidate eotaxin gene; (c) expressing the candidate eotaxin gene within the tissue sample; and (d) determining whether the tissue sample elicits a eotaxin mediated response or decrease thereof, whereby a response identifies an eotaxin gene.

In another aspect, the invention features a method of detecting a eotaxin gene in a cell involving: (a) contacting the eotaxin gene or a portion thereof greater than 9 nucleic acids, preferably greater than 18 nucleic acids in length with a preparation of genomic DNA from the cell under hybridization conditions providing detection of DNA sequences having about 50% or greater sequence identity to the conserved DNA sequences of FIG. 3A, (SEQ ID NO:5), FIG. 7 (SEQ ID NO:15), or FIG. 12A (SEQ ID NO:17), FIG. 12B (SEQ ID NO:19), and FIG. 12C (SEQ ID NO:21) or the sequences which are conserved among eotaxins relative to other proteins, as deduced from the polypeptide sequences provided in FIG. 3B (SEQ ID NOS:7–14) and FIG. 13 (SEQ ID NOS:23–25). Preferably, the region of sequence identity used for hybridization is the region of 9 nucleic acids or more encoding the region of highest conservation between the sequences shown in FIGS. 13 SEQ ID NOS:23–25) or among eotaxins in FIG. 3B (SEQ ID NOS:7–14).

In another aspect, the invention features a method of producing an eotaxin polypeptide which involves: (a) providing a cell transformed with DNA encoding an eotaxin polypeptide positioned for expression in the cell (for example, present on a plasmid or inserted in the genome of the cell); (b) culturing the transformed cell under conditions for expressing the DNA; and (c) isolating the eotaxin polypeptide.

In another aspect, the invention features substantially pure eotaxin polypeptide. Preferably, the polypeptide includes a greater than 50 amino acid sequence substantially identical to a greater than 50 amino acid sequence shown in the FIG. 3A (SEQ ID NO:6), FIG. 7 (SEQ ID NO:16), or FIG. 12A (SEQ ID NO:18), FIG. 12B (SEQ ID NO:20), and FIG. 12C (SEQ ID NO:22) more preferably the identity is to one of the conserved regions of homology shown in FIG. 3B (SEQ ID NOS: 7–14) or FIG. 13 (SEQ ID NOS: 23–25).

In another aspect, the invention features a recombinant polypeptide capable of mediating eosinophil chemotactic events wherein the polypeptide includes a domain having a sequence which has at least 70% identity to at least one of the sequences of FIG. 3A (SEQ ID NO:6), FIG. 7 (SEQ ID NO:16), or FIG. 12A (SEQ ID NO:18), FIG. 12B (SEQ ID NO:20), and FIG. 12C (SEQ ID NO:22). Preferably, the identity is to the sequence in either FIG. 12A (SEQ ID NO:18), FIG. 12B (SEQ ID NO:20), or FIG. 12C (SEQ ID NO:22). More preferably, the region of identity is 80% or greater; most preferably the region of identity is 95% or greater.

In another aspect, the invention features a method of increasing eosinophil chemotactic events wherein the method involves: (a) providing the eotaxin gene under the control of a promoter providing controllable expression of the eotaxin gene in a cell wherein the eotaxin gene is expressed in a construct capable of delivering an eotaxin protein in an amount effective to increase the eosinophil chemotactic events. The polypeptide may also be provided directly, for example, in cell culture and therapeutic uses. In preferred embodiments, eotaxin is delivered by expression of the eotaxin gene using a tissue-specific or cell type-specific promoter, or by a promoter that is activated by the introduction of an external signal or agent, such as a chemical signal or agent. In another preferred embodiment, eotaxin is delivered together with at least one other cytokine, for example, IL-4, IL-5 or both IL-4 and IL-5 together.

In preferred embodiments, the method is used for improving prognosis in patients with tumors. The method includes providing eotaxin in the region of the tumor either by providing an eosinophil attracting amount of the polypeptide or by providing an eosinophil-attracting amount of a transgene expressing the polypeptide. In one such embodiment the tumor is a solid tumor, e.g. lymphoma (e.g., Hodgkin's), plasmacytoma, carcinoma (e.g., gastric, colonic, and lung carcinomas), melanoma, and sarcoma.

In another aspect, the invention features a method of reducing inflammation and cytotoxic damage caused by eosinophils. For example, damage occurring during asthmatic reactions, eosinophilic pneumonia, chronic obstructive pulmonary disease, bronchiectasis, cystic fibrosis, inflammatory bowel diseases (i.e., Crohn's Disease and ulcerative colitis), eosinophilic colitis, allergic bronchiopulmonary aspergellolis, atopic dermatitis, urticaria, vasculitis (e.g., Churg-strauss disease), allergic conjunctivitis, allergic rhinitis, iatrogenic eosinophilia (e.g., responses to antibiotics and cytokine treatments such as interleukin-2 therapy), parasitic infections, idiopathic hypereosinophilic syndrome, eosinophil myalgia syndrome, eosinophil fascitis, and eosinophil cardiac disease. The method includes inhibiting eosinophil chemotaxis normally caused by eotaxin's eosinophil attracting biological activity. Preferably, eotaxin activity is reduced using an agonist such as an anti-eotaxin antibody or eotaxin fragment. In some embodiments, the antagonist is an eotaxin polypeptide having a deletion of 1–10 N-terminal amino acids (preferably amino acids 2–8) or having an addition of 3–10 amino acids on the amino terminus (preferably 5 amino acids). Where amino acids are added they may be random or they may be selected to have particular biological properties such as stability or hydrophilicity.

In another aspect, the invention features a method of modulating histamine release via the modulation of eotaxin activity or expression. Such modulation may be accomplished using the methods described herein. For example lowering eotaxin activity may be done to decrease histamine release which occurs during anaphylaxis, urticaria, allergic conjunctivitis, allergic rhinitis.

In another aspect, the invention features a purified antibody which binds specifically to a murine or human eotaxin protein. Such an antibody may be used in any standard immunodetection method for the identification of an Eotaxin polypeptide. Such an antibody may also be used to inhibit eotaxin protein function and to predict prognosis in following tumor diagnosis. In various embodiments, the antibody may be an intact monoclonal or polyclonal antibody, but may also be an immunologically-active antibody fragment, such as an Fab' or (Fab')$_2$ fragment, or a genetically engineered Fv fragment (see U.S. Pat. No. 4,946,788, hereby incorporated by reference).

In another aspect, the invention features a DNA sequence substantially identical to the DNA sequence shown FIG. 12A (SEQ ID NO:17), FIG. 12B (SEQ ID NO:19), and FIG. 12C (SEQ ID NO:21). In all related aspects, the invention features DNA substantially identical to the DNA sequence shown in FIG. 3A (SEQ ID NO:5) and FIG. 7 (SEQ ID NO:15).

In another aspect, the invention features a substantially pure polypeptide having a sequence substantially identical to an amino acid sequence shown in FIG. 12A (SEQ ID NO:18), FIG. 12B (SEQ ID NO:20), or FIG. 12C (SEQ ID NO:22) and in a related aspect the invention features a substantially pure polypeptide having the sequence shown in FIG. 3A (SEQ ID NO:6), FIG. 7 (SEQ ID NO:16), or FIG. 12A (SEQ ID NO:18), FIG. 12B (SEQ ID NO:20), and FIG. 12C (SEQ ID NO:22).

In another aspect, the invention features an eotaxin polypeptide which has a deletion of 1–10 amino acids at the amino terminus of the mature eotaxin polypeptide (i.e., having the signed sequence cleaved). Preferably, the deletion is of amino acids 2–8 of the mature eotaxin polypeptide. In a related aspect, the invention features eotaxin polypeptides having 3–10 amino acids added to the amino terminus of the mature polypeptide. In preferred embodiments, 5 amino acids are added.

In related aspects, the invention features substantially pure nucleic acid encoding the truncated and augmented eotaxin polypeptides of the immediately foregoing paragraph.

In another aspect, the invention features a kit for detecting compounds which modulate eotaxin mediated events. The kit includes eotaxin-encoding DNA positioned for expression in a cell capable of producing a detectable eotaxin response. By eotaxin response is meant those eotaxin mediated events described herein, particularly in the examples, below.

In a related aspect, the invention features a method for detecting a compound which alters eotaxin mediated events. The method includes: i) a cell having eotaxin encoding DNA positioned for expression; ii) contacting said cell or extracts therefrom with the compound to be tested; iii) monitoring said cell or extracts therefrom for the ability to alter eotaxin mediated events, for example increased eosinophil chemotaxis.

"Eotaxin gene" means a gene encoding a polypeptide having the eotaxin eosinophil chemoattractant characteristics or other eotaxin biological activities described herein below. An eotaxin gene is a gene encoding an eotaxin polypeptide having about 60% or greater, more preferably 70% or greater amino acid sequence identity to at least one of the eotaxin polypeptide sequences of FIG. 3A, FIG. 7, or FIG. 12, or a portion thereof. For example, the gene may encode human or murine eotaxin polypeptide. An eotaxin gene may also be defined as encoding a polypeptide with at least 50% of the activity of the eotaxin polypeptides described below (preferably, such a comparison done using assay components derived from the species from which the eotaxin polypeptide to be tested is derived. Preferably, the eotaxin gene is a murine or human eotaxin gene.

"Enhancing eosinophil chemotaxis" means increasing the number of eosinophils in the target tissue by at least 20% relative to an untreated control tissue of similar type. Preferably, the increase in the number of eosinophils is at least two-fold.

"Inhibiting eosinophil chemotaxins" means decreasing the number of eosinophils in the target tissue by at least 20% relative to an untreated control tissue of similar type. Preferably, the decrease in the number of eosinophils is at least two-fold.

"Polypeptide" means any chain of amino acids, regardless of length or post-translational modification (e.g., glycosylation or phosphorylation).

"Substantially identical" means a polypeptide or nucleic acid exhibiting at least 60%, preferably 70%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

"Substantially pure polypeptide" means an eotaxin polypeptide (or other polypeptide described herein) which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight eotaxin polypeptide. A substantially pure polypeptide may be obtained, for example, by extraction from a natural source (e.g., a mammalian cell); by expression of a recombinant nucleic acid encoding an the polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

"Substantially pure DNA" means DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

"Transformed cell" means a cell into which (or into an ancestor of which) has been introduced, by means of recombinant DNA techniques, a DNA molecule encoding (as used herein) a polypeptide described herein (for example, an eotaxin polypeptide).

"Positioned for expression" means that the DNA molecule is positioned adjacent to a DNA sequence which directs transcription and translation of the sequence (i.e., facilitates the production of, e.g., an eotaxin polypeptide, a recombinant protein or a RNA molecule).

"Promoter" means minimal sequence sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

"Operably linked" means that a gene and a regulatory sequence(s) are connected in such a way as to permit gene expression when the appropriate molecules (e.g., transcriptional activator proteins) are bound to the regulatory sequence(s).

"Transgene" means any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

"Transgenic" means any cell which includes a DNA sequence which is inserted by artifice into a cell and becomes part of the genome of the organism which develops from that cell or an animal in which a gene has been inactivated by artifice. As used herein, the transgenic organisms are generally transgenic rodents and the DNA (transgene) is inserted by artifice into the nuclear genome or in which a gene has been inactivated.

"Conserved region" means any stretch of six or more contiguous amino acids exhibiting at least 30%, preferably 50%, and most preferably 70% amino acid sequence identity between two or more of the eotaxin family members.

"Detectably-labelled" means any means for marking and identifying the presence of a molecule, e.g., an oligonucleotide probe or primer, a gene or fragment thereof, or a cDNA molecule. Methods for detectably-labelling a molecule are well known in the art and include, without limitation, radioactive labelling (e.g., with an isotope such as $^{32}P$ or $^{35}S$) and nonradioactive labelling (e.g., chemiluminescent labelling, e.g., fluorescein labelling). "Transformation" means any method for introducing foreign molecules into a cell. For example, molecules may be introduced using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., chloroplasts and mitochondria), bacteria, yeast, fungi, algae, and animal tissue.

"Purified antibody" means antibody which is at least 60%, by weight, free from proteins and naturally-occurring organic molecules with which it is naturally associated. Preferably, the preparation is at least 75%, more preferably 90%, and most preferably at least 99%, by weight, antibody, e.g., an eotaxin-specific antibody. A purified eotaxin antibody may be obtained, for example, by affinity chromatography using recombinantly-produced eotaxin protein or conserved motif peptides and standard techniques.

"Modulatory compound", as used herein, means any compound capable of either increasing eotaxin expression (i.e., at the level of transcription, translation, or post-translation) or increasing eotaxin protein activity (i.e., the amount of activity, for example, eosinophil chemotaxis, per unit of eotaxin protein).

Other features and advantages of the invention will be apparent from the following description of the preferred embodiments thereof, and from the claims.

DETAILED DESCRIPTION

The drawings will first be described.
Drawings
FIG. 1. shows the structure of murine eotaxin gene. A linear map of a 129SV genomic clone containing the eotaxin gene is indicated. Exon 1 is within a 5 kb region between XhoI and EcoRI. Exon 2 & most of exon 3 are contained within a 1.4 kb EcoRV fragment. A repeat containing 18 CA dinucleotides is indicated between exons 2 and 3. Below is the corresponding mRNA with the positions of the start (ATG) codon, stop codon (TAA), and site for signal peptidase cleavage (arrow).

FIGS. 2A and 2B show CA dinucleotide polymorphism and chromosomal mapping of murine eotaxin gene. FIG. 2A shows use of PCR primers flanking the (CA)n repeat were used to amplify DNA from the eotaxin 129SV clone (FIG. 1), or genomic DNA from C57BL/6J, DBA/2J, or Mus. spretus. As a negative control, no DNA was added in the far right lane. The 100 bp ladder (left lane) was used as molecular weight markers. FIG. 2B shows the mouse chromosome 11 map. The right panel is the location of the eotaxin gene using the backcross panel (BSS) containing approximately 1500 loci. The left panel is the Chromosome Committee Consensus map (Lossie et al. (1994) Mamm.

Gen. 5, S164–180). Other C-C chemokines are shown and referred to as small inducible cytokines, Scya1-6. Eotaxin has been assigned the name Scya11.

FIGS. 3A and 3B. FIG. 3A shows the nucleotide sequence and predicted amino acid translation of full length murine eotaxin cDNA. The arrow indicates the predicted site for signal peptide cleavage. The underlined protein sequence corresponds to predicted mature eotaxin protein. The asterisks indicate the intron/exon borders. The hatched bars overlie the ATTTA sequences that has been reported to decrease mRNA stability. The open box indicates the poly adenylation signal. FIG. 3B (SEQ ID NO:7–14) shows, alignment of murine eotaxin protein with guinea pig eotaxin and other MCPs. The boxed amino acids are identical between different proteins. The position of the leader sequence cleavage site is indicated with the arrow. The conservation of amino acid gaps in murine and guinea pig eotaxin are indicated with O*O. The positions of lysine conservations are indicated with O+O.

FIGS. 4A and 4B show chemotactic response of murine eosinophils to murine eotaxin. The chemotactic response to eotaxin was determined using increasing concentrations of supernatant from eotaxin transfected J558L cells (FIG. 4A) or COS cells (FIG. 4B). As controls, eosinophils were exposed to buffer alone, PAF (10-7 M), or 1000 ng/ml recombinant murine MIP1a (FIG. 4). The supernatant from untransfected cells is shown as control.

FIG. 5 shows northern analysis of total RNA from mouse organs. 10 mcg of total RNA from FVB/N (first nine lanes) and C57BL/6 mouse strains.

FIGS. 6A to 6C show eotaxin mRNA expression. FIG. 6A shows eotaxin mRNA following transplantation of IL-4 transfected tumors. FIG. 6 shows representative autoradiographic data from untreated mice (lanes a–e), or mice that were injected with untransfected tumor cells (CNTL) lanes f–i or IL-4 transfected tumor cells (lanes j–m) 24 hrs prior to RNA extraction from skin samples. Eotaxin and 28S mRNA bands are shown from separate mice in each lane. An eotaxin cDNA probe that was limited to the coding region was used as a probe and autoradiographs were exposed for 3 days. FIG. 6C shows eotaxin mRNA levels in murine endothelial cells. 10 mcg of total RNA prepared from untreated endothelial cells (left lane) or following treatment with 200 U/ml recombinant murine IFN-γ for 6 and 18 hrs, respectively.

FIG. 7 shows nucleotide sequence (SEQ ID NO: 15) and predicted amino acid translation (SE ID NO: 16) of full length guinea pig eotaxin cDNA. The underlined protein sequence corresponds to the sequence of mature active eotaxin isolated from the bronchoalveolar fluid except for the boxed amino acids which were previously ambiguous (Rowe et al., (1994) Mamm. Gen. 5:253–274). The arrow indicates the predicted site for signal peptide cleavage. The hatched bars overlie the ATTTA sequences that has been reported to decrease mRNA stability. These sequence data are available from EMBL/GenBank/DDBJ under accession number U18941.

FIG. 8 shows guinea pig and mouse genomic analysis. Guinea pig genomic DNA was digested with EcoR1 (Lane a) and PvuII (Lane b) and mouse genomic DNA was digested with EcoRV (Lane c). After electrophoresis and transfer to nylon membranes, a guinea pig eotaxin probe limited to the coding region of the cDNA was hybridized and washed under low stringency conditions. X-ray film was exposed for 2 weeks. Molecular weight markers (in kb) are shown to the left for lanes a & b and to the right for lane c.

FIG. 9 shows northern analysis of total RNA from various guinea pig organs. Hybridization and washing were performed under conditions of high stringency using a guinea pig eotaxin probe that was limited to the coding region of the cDNA.

FIG. 10 shows northern analysis of poly A RNA (2 mcg/lane) isolated from the lungs of guinea pigs challenged 3 hrs earlier with saline (lanes a–f) or OVA (lanes g–l). Each lane is RNA from a separate animal. Hybridization was performed with a guinea pig eotaxin probe (upper panel) or a guinea pig β-actin probe (lower panel).

FIG. 11 shows eotaxin mRNA levels following OVA challenge. OVA sensitized or saline exposed guinea pigs were challenged with aerosolized OVA or saline, respectively, and eotaxin mRNA levels in the lungs were examined.

FIGS. 12A, 12B, and 12C show the human eotaxin nucleotide sequence (SEQ ID NOS: 17, 19, and 21) and polypeptide sequence (SEQ ID NOS: 18, 20, and 22) and FIG. 12D depicts the contiguous nucleotide (SE ID NO: 26) and polypeptide sequence (SEQ ID NO: 27) of human eotaxin.

FIG. 13 shows a comparison of the human, guinea pig, and murine polypeptide sequences.

I. Introduction

Figure 1:
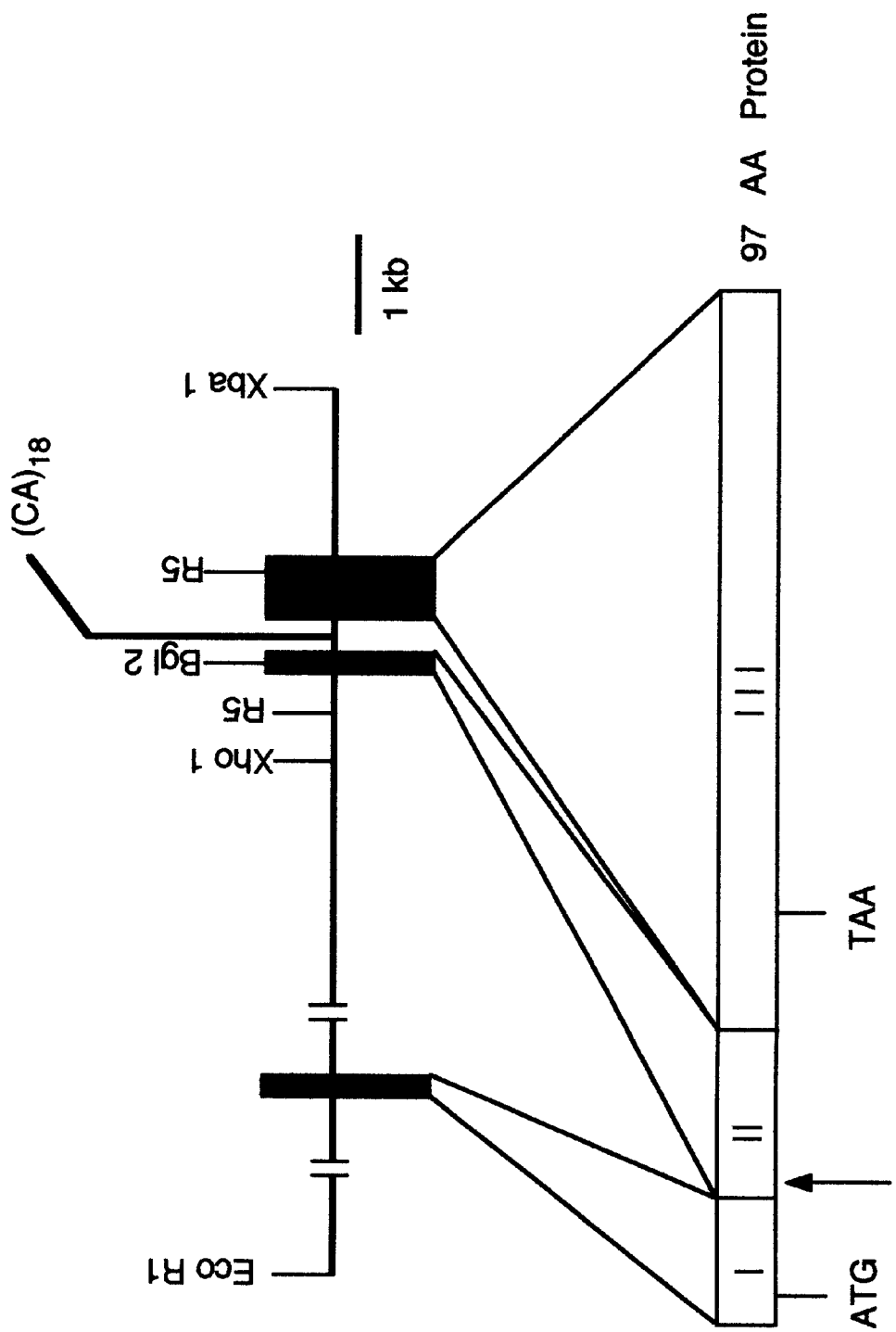

Unlike previously described chemokines active on eosinophils, eotaxin a recently described C-C chemokine, has been implicated as an eosinophil specific chemoattractant in a guinea pig model of allergic airway inflammation. Eotaxin appears to be unique among the chemokines since it causes the selective infiltration of only eosinophils when injected into the skin and when directly administered to the lungs of naive guinea pigs.

We initially cloned the guinea pig eotaxin gene. However, it was unclear if guinea pig eotaxin represented a homologue of a previously known chemokine, or if eotaxin is a distinct chemokine. Furthermore, the biological significance of eotaxin in animal models of non-allergic disease had not been previously examined.

Using the guinea pig eotaxin cDNA as a molecular probe, we cloned the murine and human eotaxin and examined the biological properties of the moved eotaxin polypeptides encoded by these genes.

The structural similarities between mouse and guinea pig eotaxin indicate that both are more closely related to one another than to other members of the C-C family of chemokines. The human sequence further affirms this observation. For example, each contains several unique features including a gap of two amino acids near the amino-end of the protein and the conservation of basic amino acids near the carboxy-end that distinguish it from other C-C chemokines. In sum, this comparison indicates that eotaxin is a distinct cytokine and not a homologue of one of the previously known members of the chemokine family. In addition, we have determined that eotaxin resides on mouse chromosome 11 in a region encoding other members of the C-C chemokine family. It is interesting that IL-4 and IL-5 also map to murine chromosome 11, however, these interleukins are not syntonic in man with the C-C chemokine locus (Lossie, et al. (1994) Mamm. Gen. 5, S164–180).

We demonstrate here that murine and human eotaxin have biologic properties that are comparable to those of the guinea pig homologue. We further demonstrate that the expression of eotaxin is consistent with a causative role in human disease. In order to demonstrate direct eosinophil chemotactic activity, we isolated eosinophils from IL-5 transgenic mice (Dent, et al. (1990) J. Exp. Med. 172, 1425–1431) and measured eosinophil chemotaxis in-vitro. It is important to note that, despite the fact that there are large numbers of eosinophils in the hematopoietic organs of these IL-5 transgenic mice, there are few eosinophils in other tissues and these transgenic mice are quite healthy Dent, et al., Id.). This benign phenotype suggests that other signals (in addition to IL-5) are necessary for eosinophil tissue recruitment and activation.

Using eosinophils from this system, we showed that recombinant mouse eotaxin is a powerful chemoattractant for eosinophils, as are murine MIP-1a and PAF which were used as positive controls. No chemoattractive activity was seen for eotaxin on macrophages or neutrophils. However, these cells may have been desensitized since they had already migrated into an inflamed peritoneal cavity in-vivo. Neither MIP-1a or PAF are active solely on eosinophils making it difficult to use them to develop clinically useful antagonists against eosinophils (Resnick, et al. (1993) Amer. J. Resp. Cell. Mol. Biol. 8, 349–355; Rot, et al. (1992) J. Exp. Med 176, 1489–1495).

The biological properties which can now attribute to eotaxin based on our murine data make it likely that there will be a similar activity and thus pharmacological utility, in humans. It is likely that the eosinophils isolated from the IL-5 transgenic mice have been primed in-vivo by IL-5 exposure and this potentiates their responsiveness to eotaxin. Consistent with this, IL-5 activates human eosinophils and primes them to respond to RANTES in-vitro (Rothenberg, et al. (1989) J. Immun. 143, 2311–2316; Ebisawa, et al. (1994) J. Immun. 153, 2153–2160). Accordingly, we proved the human eotaxin gene and polypeptide for use as therapeutics and for the isolation compounds which block eosinophil chemotaxis.

Murine eotaxin mRNA is constitutively expressed in mucosal tissues where eosinophils normally reside (skin, lung and intestinal tract). Nonetheless, expression is also seen in thymus, lymph node, and muscle where resident eosinophils are rare. This pattern of mRNA tissue distribution is similar to that previously seen in guinea pig, although mice have higher expression in the thymus and skin while guinea pigs have higher expression in the lung (Rothenberg, et al. (1995) J. Exp. Med. 181, 1211–1216). This is consistent with the fact that guinea pigs have high basal numbers of eosinophils in the lungs, while pulmonary eosinophils are undetectable in healthy mice. Such observations are further consistent with a role for eotaxin in promoting eosinophil pulmonary homing.

The expression of eotaxin in the skin has implications for human cutaneous disease since there are many disorders characterized by excessive infiltration and activation of skin eosinophils (e.g. atopic dermatitis, urticaria, bullous pemphigoid, etc.) (Leiferman, K. M. (1991) J. Am. Acad. Derm. 24, 1101–1112).

Without wishing to bind ourselves to particular theory, we note that our studies also offer a potential explanation for the observation that eosinophils infiltrate a variety of human tumors, an observation that is generally associated with an improved prognosis for such patients (Iwasaki, et al. (1986) Cancer 58, 1321–1327; Pretlow, et al. (1983) Cancer Res. 43, 2997–3000). As noted above, the elaboration of IL-4 by a tumor transplant induces a potent anti-tumor effect which is mediated by infiltrating eosinophils (Tepper, et al. (1989) Cell 57, 503–512; Tepper, R. I., Coffman, R. L. & Leder, P. (1992) Science 257, 548–551). We have also shown that eotaxin mRNA is induced at the site of the IL-4-transfected tumor cell transplant. Thus, eotaxin appears to be the critical eosinophil chemoattractant that, in part, mediates eosinophil tissue recruitment in this process. In addition, it may be concluded that eotaxin is involved in other disease states mediated by IL-4 (e.g. asthma). Accordingly, this finding allows us to provide therapies for these conditions.

As we have noted, the mechanism of IL-4-mediated eosinophil accumulation in the tumor model and in allergic models is not completely understood. It is likely that IL-4 works in conjunction with other accessory cells to induce eosinophil recruitment. Consistent with this, IL-4 is known to induce the expression of the eosinophil endothelial cell adhesion receptor (VCAM-1) (Schleimer, et al. (1992) J. Immun. 148, 1086–1092) and to promote the production of Th2 cells which elaborate IL-5. However, treatment of mice with neutralizing antibodies against VCAM-1 or IL-5 does not completely block eosinophil infiltration into tumor cells (Tepper, et al. (1992) Science 257, 548–551; Tepper, (1994) J. All. Clin. Immun. 94, 1225–1231). In contrast, IFN-γ production is increased in this process and treatment of mice with antibodies that neutralize IFN-∂ does prevent tumor killing (Platzer, et al. (1992) Eur. J. Immun. 22, 1729–1733). The cellular source of eotaxin mRNA found following IL-4 tumor cell transplantation is not known, but we have seen that treatment of endothelial cells with IFN-γ induces expression of eotaxin mRNA. This raises the possibility that IL-4 may be inducing eotaxin mRNA by first inducing IFN-γ in the IL-4 tumor model. These findings underscore the potential involvement of eotaxin in multiple immune responses, involving IL-4 and/or IFN-γ.

II. Eotaxin Protein Expression

In general, eotaxin proteins according to the invention may be produced by transformation of a suitable host cell with all or part of a eotaxin-encoding cDNA fragment (e.g., the cDNA described above) in a suitable expression vehicle.

Those skilled in the field of molecular biology will understand that any of a wide variety of expression systems may be used to provide the recombinant protein. The precise host cell used is not critical to the invention. The eotaxin protein may be produced in a prokaryotic host (e.g., *E. coli*) or in a eukaryotic host (e.g., *Saccharomyces cerevisiae*, insect cells, e.g., Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

One preferred expression system is the baculovirus system (using, for example, the vector pBacPAK9) available from Clontech (Pal Alto, Calif.). If desired, this system may be used in conjunction with other protein expression techniques, for example, the myc tag approach described by Evan et al. (Mol. Cell Biol. 5:3610–3616, 1985).

Alternatively, an eotaxin protein is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the eotaxin protein is cloned into an expression vector which includes the dihydrofolate reductase (DHFR) gene. Integration of the plasmid and, therefore, the eotaxin protein-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR$^-$ cells, ATCC Accession No. CRL 9096) are among the host cells preferred for DHFR selection of a stably-transfected cell line or DHFR-mediated gene amplification.

Once the recombinant eotaxin protein is expressed, it is isolated, e.g., using affinity chromatography. In one example, an anti-eotaxin protein antibody (e.g., produced as described herein) may be attached to a column and used to isolate the eotaxin protein. Lysis and fractionation of eotaxin protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short eotaxin protein fragments, can also be produced by chemical synthesis (e.g., by the methods described in *Solid Phase Peptide Synthesis,* 2nd ed., 1984 The Pierce Chemical Co., Rockford, Ill.).

These general techniques of polypeptide expression and purification can also be used to produce and isolate useful eotaxin fragments or analogs (described herein).

III. Anti-Eotaxin Antibodies

To generate eotaxin-specific antibodies, an eotaxin coding sequence (i.e., amino acids 180–276) was expressed as a C-terminal fusion with glutathione S-transferase (GST) (Smith et al., Gene 67:31–40, 1988). The fusion protein (which was shown to be of the predicted size) was purified on glutathione-Sepharose beads, eluted with glutathione cleaved with thrombin (at the engineered cleavage site), and purified to the degree necessary for immunization of rabbits. Primary immunizations are carried out with Freund's complete adjuvant and subsequent immunizations with Freund's incomplete adjuvant. Antibody titres are monitored by Western blot and immunoprecipitation analyses using the thrombin-cleaved eotaxin protein fragment of the GST-eotaxin fusion protein. Immune sera are affinity purified using CNBr-Sepharose-coupled eotaxin protein. Antiserum specificity is determined using a panel of unrelated GST proteins (including GSTp53, Rb, HPV-16 E6, and E6-AP) and GST-trypsin (which was generated by PCR using known sequences).

As an alternate or adjunct immunogen to GST fusion proteins, peptides corresponding to relatively unique hydrophilic regions of eotaxin may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots using peptide conjugates, and by Western blot and immunoprecipitation using eotaxin expressed as a GST fusion protein.

Alternatively, monoclonal antibodies may be prepared using the eotaxin proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981; Ausubel et al., supra). Once produced, monoclonal antibodies are also tested for specific eotaxin recognition by Western blot or immunoprecipitation analysis (by the methods described in Ausubel et al., supra). Antibodies which specifically recognize eotaxin are considered to be useful in the invention; such antibodies may be used, e.g., in an immunoassay to monitor the level of eotaxin produced by a mammal (for example, to determine the amount or location of eotaxin).

Preferably, antibodies of the invention are produced using the whole eotaxin polypeptide, but using fragments of the eotaxin polypeptide which lie outside highly conserved regions and appear likely to be antigenic, by criteria such as high frequency of charged residues may also be used. In one specific example, such fragments are generated by standard techniques of PCR and cloned into the pGEX expression vector (Ausubel et al., supra). Fusion proteins are expressed in *E. coli* and purified using a glutathione agarose affinity matrix as described in Ausubel et al. (supra). To attempt to minimize the potential problems of low affinity or specificity of antisera, two or three such fusions are generated for each protein, and each fusion is injected into at least two rabbits. Antisera are raised by injections in a series, preferably including at least three booster injections.

IV. Identification and Administration of Molecules that Modulate Eotaxin Protein Expression Isolation of the eotaxin cDNA also facilitates the identification of molecules which increase or decrease eotaxin expression. According to one approach, candidate molecules are added at varying concentrations to the culture medium of cells expressing eotaxin mRNA. Eotaxin expression is then measured, for example, by standard Northern blot analysis (Ausubel et al., supra) using a eotaxin cDNA (or cDNA fragment) as a hybridization probe. The level of eotaxin expression in the presence of the candidate molecule is compared to the level measured for the same cells in the same culture medium but in the absence of the candidate molecule.

If desired, the effect of candidate modulators on expression may, in the alternative, be measured at the level of eotaxin protein production using the same general approach and standard immunological detection techniques, such as Western blotting or immunoprecipitation with a eotaxin-specific antibody (for example, the eotaxin antibody described herein).

Candidate modulators may be purified (or substantially purified) molecules or may be one component of a mixture of compounds (e.g., an extract or supernatant obtained from cells; Ausubel et al., supra). In a mixed compound assay, eotaxin expression is tested against progressively smaller subsets of the candidate compound pool (e.g., produced by standard purification techniques, e.g., HPLC or FPLC) until a single compound or minimal compound mixture is demonstrated to modulate eotaxin expression.

Alternatively, or in addition, candidate compounds may be screened for those which modulate eotaxin eosinophil activity. In this approach, chemotaxis activity in the presence of a candidate compound is compared to chemotaxis activity in its absence, under equivalent conditions. Again, such a screen may begin with a pool of candidate compounds, from which one or more useful modulator compounds are isolated in a step-wise fashion. Chemotaxis of eosinophils activity may be measured by any standard assay, for example, those described herein.

Candidate eotaxin modulators include peptide as well as non-peptide molecules (e.g., peptide or non-peptide molecules found, e.g., in a cell extract, mammalian serum, or growth medium on which mammalian cells have been cultured). Particularly useful modulators of eotaxin expression include tumor necrosis factor-a, interleukin-1 α and β, and gamma interferon.

A molecule which promotes a decrease in eotaxin expression or eotaxin eosinophil chemotaxis activity is considered particularly useful in the invention; such a molecule may be used, for example, as a therapeutic to decrease cellular levels of eotaxin and thereby decrease the pathology caused by excessive eosinophils. For example, asthmatic reactions, chronic obstructive pulmonary diseases, bronchiectasis, cystic fibrosis, inflammatory bowel diseases (i.e., Crohn's Disease and ulcerative colitis), eosinophilic pneumonia, eosinophilic colitis, and parasitic infections may be treated using a molecule which inhibits eotaxin expression or eotaxin biological activity.

A molecule which enhances eotaxin activity may be used in the treatment of tumors.

Modulators found to be effective at the level of eotaxin expression or activity may be confirmed as useful in animal models (i.e., the mouse tumor model or the guinea pig lung model) and, if successful, may be used as anti-cancer or anti-inflammatory therapeutics.

A eotaxin modulator may be administered with a pharmaceutically-acceptable diluent, carrier, or excipient, in unit dosage form. Conventional pharmaceutical practice may be employed to provide suitable formulations or compositions to administer eotaxin to patients suffering from or presymptomatic for a eotaxin-associated carcinoma. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for NES1 modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a NES1 modulatory compound may be combined with more traditional cancer therapies such as surgery, radiation, or chemotherapy.

V. Detection of an Eosinophil Chemotaxis Condition

Eotaxin polypeptides and nucleic acid sequences find diagnostic use in the detection or monitoring of eosinophil mediated conditions. In particular, because eotaxin is involved in eosinophil chemotaxis and because the presence of eosinophils correlates with an improved prognosis for humans with tumors, an alteration in the level of eotaxin production provides an indication of the prognosis of the condition. Levels of eotaxin expression may be assayed by any standard technique. For example, its expression in a biological sample (e.g., a biopsy) may be monitored by standard Northern blot analysis or may be aided by PCR (see, e.g., Ausubel et al., supra; *PCR Technology: Principles and Applications for DNA Amplification*, ed., H. A. Ehrlich, Stockton Press, NY; and Yap and McGee, Nucl. Acids. Res. 19:4294, 1991).

In yet another approach, immunoassays are used to detect or monitor eotaxin protein in a biological sample eotaxin-specific polyclonal or monoclonal antibodies (produced as described above) may be used in any standard immunoassay format (e.g., ELISA, Western blot, or RIA assay) to measure eotaxin polypeptide levels; again comparison is to wild-type eotaxin levels, and a decrease in eotaxin production is indicative of a poor prognosis. Examples of immunoassays are described, e.g., in Ausubel et al., supra. Immunohistochemical techniques may also be utilized for eotaxin detection. For example, a tissue sample may be obtained from a patient, and a section stained for the presence of eotaxin using an anti-eotaxin antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

VI. Eotaxin Therapy

Because expression of eotaxin correlates with eosinophil chemotaxis and improved tumor prognosis, the eotaxin gene also finds use in anti-cancer gene therapy. In particular, to enhance eosinophil infiltration of a tumor, a functional eotaxin gene may be introduced into cells at the site of a tumor. Alternatively, eotaxin polypeptides which alterations which block eotaxin activity may be administered via gene therapy for the treatment of eosinophil mediated inflammatory conditions.

Retroviral vectors, adenoviral vectors, adeno-associated viral vectors, or other viral vectors with the appropriate tropism for eotaxin-expressing cells (for example, mucosal or endothelial cells) may be used as a gene transfer delivery system for a therapeutic eotaxin gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, Current Opinion in Biotechnology 1:55–61, 1990; Sharp, The Lancet 337:1277–1278, 1991; Cornetta et al., Nucleic Acid Research and Molecular Biology 36:311–322, 1987; Anderson, Science 226:401–409, 1984; Moen, Blood Cells 17:407–416, 1991; and Miller and Rosman, Biotechniques 7:980–990, 1989; Le Gal La Salle et al., Science 259:988–990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches may also be employed for the introduction of therapeutic DNA into cells. For example, eotaxin may be introduced into a tumor cell by the techniques of lipofection (Felgner et al., Proc. Natl. Acad. Sci. USA 84:7413, 1987; Ono et al., Neuroscience Lett 117:259, 1990; Brigham et al., Am. J. Med. Sci. 298:278, 1989; Staubinger and Papahadjopoulos, Meth. Enz. 101:512, 1983); asialorosonucoid-polylysine conjugation (Wu and Wu, J. Biol. Chem. 263:14621, 1988; Wu et al., J. Biol. Chem. 264:16985, 1989); or, less preferably, microinjection under surgical conditions (Wolff et al., Science 247:1465, 1990).

For any of the above approaches, the therapeutic eotaxin DNA construct is preferably applied to the site of the malignancy or inflammation and cytotoxic damage (for example, by injection), but may also be applied to tissue in the vicinity of the malignancy or inflammation and cytotoxic damage or even to a blood vessel supplying these areas.

In the gene therapy constructs, eotaxin cDNA expression is directed from any suitable promoter (e.g., the human cytomegalovirus, simian virus 40, or metallothionein promoters), and its production is regulated by any desired mammalian regulatory element. For example, if desired, enhancers known to direct preferential gene expression in endothelial or epithelial cells may be used to direct eotaxin expression. Such enhancers include, without limitation, the lung specific promoters (e.g. surfactant), and gut specific regulatory sequences.

Alternatively, if a eotaxin genomic clone is utilized as a therapeutic construct (for example, following its isolation by hybridization with the eotaxin cDNA described above), eotaxin expression is regulated by its cognate regulatory sequences or, if desired, by regulatory sequences derived from a heterologous source, e.g., any of the promoters or regulatory elements described above.

Less preferably, eotaxin gene therapy is accomplished by direct administration of the eotaxin mRNA to a tumor. This mRNA may be produced and isolated by any standard technique, but is most readily produced by in vitro transcription using a eotaxin cDNA under the control of a high efficiency promoter (e.g., the T7 promoter). Administration of eotaxin mRNA to malignant cells is carried out by any of the methods for direct nucleic acid administration described above.

Ideally, the production of eotaxin protein by any gene anti-tumor therapeutic approach described above results in a cellular level of eotaxin that is at least equivalent to the normal, cellular level of NES1 in an unaffected individual. Treatment by any NES1-mediated gene therapy approach may be combined with more traditional cancer therapies such as surgery, radiation, or chemotherapy.

Another therapeutic approach included within the invention involves direct administration of recombinant eotaxin protein, either to the site of a malignancy (for example, by injection) or systemically by any conventional recombinant protein administration technique. The actual dosage of eotaxin depends on a number of factors, including the size and health of the individual patient, but, generally, between 0.1 mg and 100 mg inclusive are administered per day to an adult in any pharmaceutically-acceptable formulation.

The above approaches may also be used to inhibit eotaxin activity by substituting an altered eotaxin polypeptide having eotaxin blocking activity (e.g., have a deletion or insertion at the amino terminus) for the eotaxin polypeptide described above.

VII. Transgenic Animals

Transgenic animals may be made using standard techniques. For example, the eotaxin gene may be provided using endogenous control sequences or using constituative, tissue-specific, or inducible regulatory sequences. Transgenic animals lacking functional eotaxin polypeptide may also be made using standard techniques. This may be done by engineering knock-out mutations in the eotaxin gene using DNA sequences provided herein.

The following examples are provided to illustrate not limit the invention.

VIII. Examples

A. Materials and Methods

Guinea Pig eotaxin cloning. Based on the published amino acid sequence of guinea pig eotaxin (Jose, et al. (1994) J. Exp. Med. 179:881–887) the following degenerate oligonucleotide primers containing EcoR1 and BamH1 restriction sites respectively were synthesized: CCGGAATTCCA(CT)CC(AGC T)GG(AGCT)AT(ACT) (128 fold degeneracy) and CGCGGATCCGC(AG)CA (AGT)AT CAT(CT)TT(AG)TC (32-fold degeneracy). First strand cDNA was synthesized from guinea pig lung RNA and PCR was performed with an initial five cycles at 370° or 60s, followed by 25 cycles at 50° for 60s (denaturation at 95° for 30s and extension at 72° for 90s) in order to amplify a 130 bp eotaxin cDNA fragment that was subsequently subcloned into Bluescript II KS (Stratagene). Construction of a cDNA library using poly A RNA isolated from the lung of an OVA sensitized guinea pig was performed using Stratagene ZAP Express Vector according to the directions of the manufacturer. 500,000 independent clones were subsequently amplified and an aliquot of this cDNA library containing 1×106 phage was screened with the 130 bp eotaxin cDNA that had been 32P-labeled with Klenow enzyme. Two phagemids were isolated and subsequently subjected to automated sequencing on both strands using Applied Biosystems Instrumentation (model 373a) and the dye- terminator protocol. Sequence analysis was performed using software developed by the University of Wisconsin genetics computer group (Altschul, et al. (1990) J. Mol. Biol. 215:403–410).

DNA and RNA analysis. RNA was isolated by CsCl centrifugation in guanidine isothiocyanate (Chirgwin, et al. (1979) Biochemistry. 18:5294–9). Isolation of biologically active ribonucleic acid from sources enriched in ribonuclease. DNA was isolated from these gradients as well. In some cases, RNA was isolated using RNAzol (Biotecx Lab, Inc.) according to the directions of the manufacturer. Poly A RNA was enriched by elution through an oligo dT column (Pharmacia). 10 mcg of total RNA, 2 mcg of poly A RNA, or 10 mcg of restriction endonuclease cut DNA was electrophoresed in agarose, and transferred to Gene Screen (NEN Dupont) membranes. Membranes were hybridized with 32P labeled full length cDNA or a fragment encoding the translated protein (bp 57–356). High stringency hybridization was performed in 50% formamide, 10% dextran sulfate, 5×SSC, 1×DenhardtOs solution (0.0002% (w/v) polyvinylpyrrolidone, 0.0002% (w/v) BSA, 0.0002% (w/v) Ficoll 400), 1% (w/v) SDS, 100 mcg/ml denatured herring sperm DNA, and 20 mM Tris at 42° C. and blots were washed with 0.2×SSC, 0.5% SDS at 65° C. Low stringency hybridization was performed in 0.6M NaCl, 80 mM TrisCl, 4 mM EDTA, 0.1% (w/v) sodium pyrophosphate, 0.1% (w/v) SDS, 10×DenhardtOs, 100 mcg/ml denatured herring sperm DNA at 50° C. and washed with 1×SSC, 0.05% SDS at 50° C. Quantitation of the intensity of band hybridization was determined using a Phosphor-Imager (Molecular Dynamics).

Guinea Pig eotaxin Gene Analysis. A cDNA probe from the coding region of guinea pig eotaxin cDNA (bp 57–356), (Rothenberg, et al. (1995) J. Exp. Med. 181, 1211–1216), was 32P-labeled with Klenow enzyme and used to screen 1×106 plaques from a mouse 129SV genomic library (Stratagene, La Jolla, Calif. ) under conditions of low stringency (hybridization in 0.6M NaCl, 80 mM TrisCl, 4 mM EDTA, 0.1% sodium pyrophosphate, 0.1% SDS, 10×DenhardtOs solution (0.002% polyvinylpyrrolidone, 0.002% BSA, 0.002% Ficoll 400), 100 mcg/ml denatured herring sperm DNA at 50° C. and blots washed with 1×SSC, 0.05% SDS at 50° C.). Two plaques hybridized strongly and were purified. The mouse genomic DNA was liberated from the phage DNA by Not I digestion and sub-cloned into pBlue- Script SK II (Stratagene). Restriction mapping indicated that the two genomic clones had overlapping regions. A 1.4 kb EcoRV genomic fragment that hybridized with guinea pig eotaxin was subcloned into pBlue-Script KS II, and subjected to automated sequencing on both strands using Applied Biosystems Instrumentation (model 373a) and the dye-terminator protocol. Sequence analysis was performed using software developed by the University of Wisconsin genetics computer group Altschul, et al. (1990) J. Mol. Biol. 215, 403–410.

Eotaxin chromosomal localization was determined by the analysis of polymorphism in the CA repeat found in intron 2. PCR primers flanking this repeat were constructed (50 sense oligonucleotide: CACCCTGAAAGCCATAGTGT and 30 antisense oligonucleotide: TGTGTACCTGGGAAATTAG) and genomic DNA was amplified by PCR. Using these primers, a size polymorphism was identified between C57BL/6J and Mus. spretus DNA and a panel of DNA from 94 interspecific backcrosses between (C57BL/6EiJ×SPRET/Ei)F1×SPRET/Ei (BSS) was genotyped by PCR, (Rowe, et al. (1994) Mamm. Gen. 5, 253–274). The resulting segregation pattern was compared to the approximately 1500 loci previously typed in this cross (Rowe, et al. (1994) Mamm. Gen. 5, 253–274). Gene order was determined by minimizing double crossovers.

Murine eotaxin cDNA Analysis. The 1.4 kb Eco RV genomic fragment was used to screen a mouse (C57BL/6× CBA) lung Uni-Zap cDNA expression library (Stratagene) under conditions of high stringency (hybridization in 50% formamide, 10% dextran sulfate, 5×SSC, 1×DenhardtOs solution, 1% SDS, 100 mcg/ml denatured herring sperm DNA, and 20 mM Tris at 42° C. and blots were washed with 0.2×SSC, 0.5% SDS at 65° C). Four positive plaques were identified, purified, and phagemids were prepared according to the instructions of the library manufacturer. The four inserts were completely sequenced on both strands by automated sequencing. Alignment analysis was determined by the Clustal method using MegAlign software (DNASTAR Inc) (Higgins, et al. (1988) Gene 73, 237–244).

Murine RNA analysis. An SV-40 immortalized murine endothelial cell line (OConnell, et al. (1990) J. Immun. 144, 521–525) was cultured in DMEM medium supplemented with 10% iron fortified calf serum with or without 200 U/ml recombinant murine IFN-∂ (Genentech, Inc., San Francisco). Mouse bone-marrow derived mast cells were obtained by culturing mouse bone marrow in the presence of 50% WEHI-3 conditioned medium for 4 weeks (Razin, et al. (1981) Proc Natl Acad Sci U.S.A. 78, 2559–2561). Cell lines (WEHI-3, P815, and RAW 264.7) were purchased from American Type Tissue Culture Collection (Rockville, Md.). In the tumor transplantation experiments, 2×106 J558L or a murine IL-4 transfected J558L cell line (I3L6) were injected s.c. into 4–6 week old Balb/c female mice (Jackson Laboratory) as previously described (Tepper, et al. (1989) Cell 57, 503–512). At various times after tumor transplantation, the local skin was treated with Nair (Carter Products, N.Y.) to remove hair, and the skin and subcutaneous tissue was excised. RNA was isolated by CsCl centrifugation in guanidine isothiocyanate (Chirgwin, et al. (1979) Biochem. 18, 5294–5299 or by using RNAzol (Biotecx Lab, Inc.)). 10 mcg of total RNA was fractionated by gel electrophoresis using 1.5% agarose and 1.9% formaldehyde, and transferred to Gene Screen (NEN Dupont) membranes. The murine MCP-1 probe is described in (Rollins, et al. (1988) Proc. Natl. Acad. Sci. U.S.A. 85, 3738–3742). High stringency hybridization and washing was performed as described above. The quantification of total RNA was determined by hybridization of a ribosomal 28S cDNA probe (Rich, et al. (1987) Mol. Cell. Biol. 7, 4065–4074). Quantitation of the intensity of band hybridization was determined using a Phosphor-Imager (Molecular Dynamics).

Construction and Transfection of Eotaxin Expression Vectors. PCR primers were designed to amplify the coding region of murine eotaxin flanked by convenient restriction sites for subsequent sub-cloning. PCR was performed under standard conditions using eotaxin cDNA-pBlueScript as a template. The resulting PCR products were subsequently subcloned using a TA cloning kit (Invitrogen, San Diego, Calif.) and confirmatory sequencing was performed. Eotaxin cDNA was subcloned into the Hind III/EcoRI sites of pcDNA-I/Amp (Invitrogen). 4 mcg of the eotaxin-pcDNA-I construct was transfected into 100 mm plates containing ~30% confluent COS cells using DEAE-Dextran (Lopata, et al. (1984) Nucl. Acids Res. 12, 5707–5717). In a replicate sample of COS cells, transfection efficiency was >50% using a CMV promoter-placental alkaline phosphatase control plasmid (Fields-Berry, et al. (1992) Proc. Natl. Acad. Sci. U.S.A. 89, 693–697). RNA expression was confirmed by Northern analysis using the murine eotaxin cDNA as a probe. Eotaxin-pcDNA-I transfected or mock transfected COS cell supernatant was obtained after 72 hrs of culture and stored at 4° C. In another set of transfection experiments, eotaxin was similarly subcloned into the HindIII/EcoRI site of MoLTR-SV40 I/PA expression vector as previously described (Luster, et al. (1993) J. Exp. Med. 178, 1057–1065). 20 mcg of linearized eotaxin-MoLTR construct and 1 mcg of linearized neomycin resistance plasmid pSV7Neo were used to transfect J558L cells by electroporation. G418 resistant cells from single wells were analyzed for eotaxin mRNA expression by Northern analysis. Cells expressing eotaxin or control untransfected cells (that do not express eotaxin) were expanded in large cultures. In order to optimize the concentration of eotaxin in the supernatant, the cells were grown at high density (1×106 cells/ml) in RPMI without FCS, cultured for 72 hrs, and the conditioned medium was concentrated 5-fold with Centricon 3000 microconcentrators (Amicon, Beverly, Mass.) before being stored at 4° C.

Chemotaxis Assays. Murine eosinophils were isolated from IL-5 transgenic mice (Dent, et al. (1990) J. Exp. Med. 172, 1425–1431). These mice develop splenomegaly with eosinophils accounting for ~30% of the splenocytes. Eosinophils were purified from the spleen using immunomagnetic separation to remove the contaminating splenocytes. Briefly, splenocytes were labeled with anti-Thy-1 (M5/49), anti-B220 (6B2), and anti-Lyt-2 (53–6.7). Hybridoma cell lines were obtained from American Type Culture Collection and hybridoma cell supernatants were used as a source of antibodies. The antibody labeled cells were treated with sheep anti-rat serum coated-magnetic beads (M450, Dynal, Great Neck, N.Y.) and eosinophils were enriched by negative selection through a magnetic field. The resulting eosinophil preparations were 85–92% pure. Macrophages cells were isolated from the peritoneal cavity of mice that had been pre-treated (2 days prior) with intraperitoneal injection of 2.9% thioglycollate (Difco, Detroit, Calif.). Peritoneal neutrophils were isolated from mice pre-treated with sodium casein (Luo, et al. (1994) J. Immun. 153, 4616–4624). Macrophages and neutrophils were purified by Percoll gradients (Luo, et al. (1994) J. Immun. 153, 4616–4624) and accounted for >90% of the cells. Eosinophils or macrophages were suspended in HBSS with 0.05% BSA at 2×106 cells/ml, respectively, and 50 ml of replicate cells were placed in the top well of a 48 well microchemotaxis chamber (Neuro Probe, Inc, Cabin John, Md.). A polycarbonate filter with 5-$\mu$m pores was used to separate the cells from buffer (30 ml) alone or buffer containing recombinant murine MIP-1a (R&D Systems, Minneapolis, Minn.), PAF (Calbiochem, La Jolla, Calif.), COS cell supernatant, or J558L supernatant. Cells were incubated at 37° C. for 60 minutes (eosinophils and neutrophils) or 90 minutes (macrophages) and the cells that migrated across the filter and adhered to the bottom side of the filter were stained with Diff-Quick (Baxter Scientific, McGaw Park, Ill.). The number of cells per 400×field were counted.

Induction of Airway Inflammation. Airway inflammation was induced in male Hartley guinea pigs (300–500 g body weight) by OVA sensitization as previously reported Lilly, et al. (1994) J. Clin. Invest. 93:2667–2674. 1994. Effects of chronic airway inflammation on the activity and enzymatic inactivation of neuropeptides in guinea pig lungs. Briefly, guinea pigs were pretreated with pyrilamine malate by i.p. injection prior to aerosolized OVA (1% w/v in 0.9% sterile sodium chloride) or saline alone. Animals were exposed in an aerosol chamber on three occasions at 7-d intervals and the lungs were harvested at various points after the final exposure. Organs were frozen in liquid nitrogen and used for subsequent RNA isolation. A guinea pig lung epithelial cell line (JH4 clone 1) and a guinea pig colon adenocarcinoma cell line (GPC-16) were purchased from American Type Tissue Culture Collection (CCL 158).

Statistical Analysis. The statistical significance of differences between means was determined by analysis of variance (ANOVA). P<0.05 was considered significant. When ANOVA indicated a significant difference, the Newman-Keuls test was used to determine which groups were significantly different from each other.

B. Analysis of Guinea Pig Eotaxin cDNA

Using degenerate oligonucleotide primers based upon the amino acid sequence of guinea pig eotaxin, a 130 bp cDNA was amplified by PCR from guinea pig lung single stranded cDNA. This PCR product encoded a peptide identical to eotaxin and was used to screen an amplified cDNA library made from the inflamed lung of an OVA-sensitized guinea pig. From sixty positive plaques, six plaques were subsequently purified and their excised phagemids had an insert size of ~700–800 bp. Sequence analysis of the longest two inserts revealed that the regions of overlap were identical. The cDNA was 818 bp long with an open reading frame that encoded 96 amino acids. The predicted protein sequence of the carboxy terminal 73 amino acids agreed exactly with the protein sequence of eotaxin isolated from guinea pig bronchoalveolar fluid (shown underlined in FIG. 7) except for three amino acids that were previously ambiguous (shown surrounded by a box in FIG. 7 (SEQ ID NO: 16)) (Jose, et al. (1994) J. Exp. Med. 179:881–887).

The 5' region of the cDNA encoded a putative hydrophobic leader sequence whose cleavage site was predicted to occur at the amino- terminal site at which the active eotaxin protein sequence starts (shown with the arrow in FIG. 7) (Von Heijne, G. (1983) Eur. J. Biochem. 133:17–21). This structure strongly suggested that eotaxin was unlikely to exist as a precursor protein requiring additional proteolytic cleavage for activation. This type of biochemical processing has been seen with the platelet basic proteins, members of the C-X-C chemokine family (Holt, et al. (1986) Biochemistry. 25:1988–96). A Kozak consensus sequence for translation initiation was identified 5' of the AUG (Kozak, M. (1987) Nucleic Acids Res. 15:8125–48). The 30 untranslated region encoded a mRNA with 59% AU nucleotides including two OAUUUAO domains (shown with the hatched lines) that have been reported to decrease the mRNA stability of other cytokine mRNAs (Shaw, et al. (1986) Cell 46:659–67).

The nucleotide sequence showed significant homology to other members of the C-C chemokine family, in particular to members of the MCP family (Van, et al. (1992) J. Exp. Med. 176:59–65). The full length cDNA was 61, 58, 42, 38, and 52% identical in nucleic acid to human MCP-3, MCP-1, MIP-1a , RANTES, and guinea pig MCP-1, respectively. Even greater homology was seen when only the region of the cDNA that encoded protein was compared (Table 1). Comparison of the leader sequence with other sequences in the gene data bank revealed that the eotaxin leader sequence was homologous only to other leader sequences of the MCP family (81 and 74% nucleotide identity and 78 and 70% amino acid identity to human MCP-3 and MCP-1, respectively). This level of homology suggested that these leader sequences may have an additional biological role, perhaps in cellular targeting (e.g. localization to a granule sub-compartment). Comparison of the homology to other C-C chemokines revealed that the nucleotide identity was almost always greater than the amino acid identity and similarity (Table 1). Although the MCPs were initially characterized by their ability to activate and attract macrophages, MCP-3 has been reported to cause eosinophil chemotaxis (Dahinden, et al. (1994) J. Exp. Med. 179:751–756; Biochem. Biophys. Res. Commun. 201:493–499).

C. Eotaxin Gene in the Guinea Pig and Mouse Genome

Figure 8:
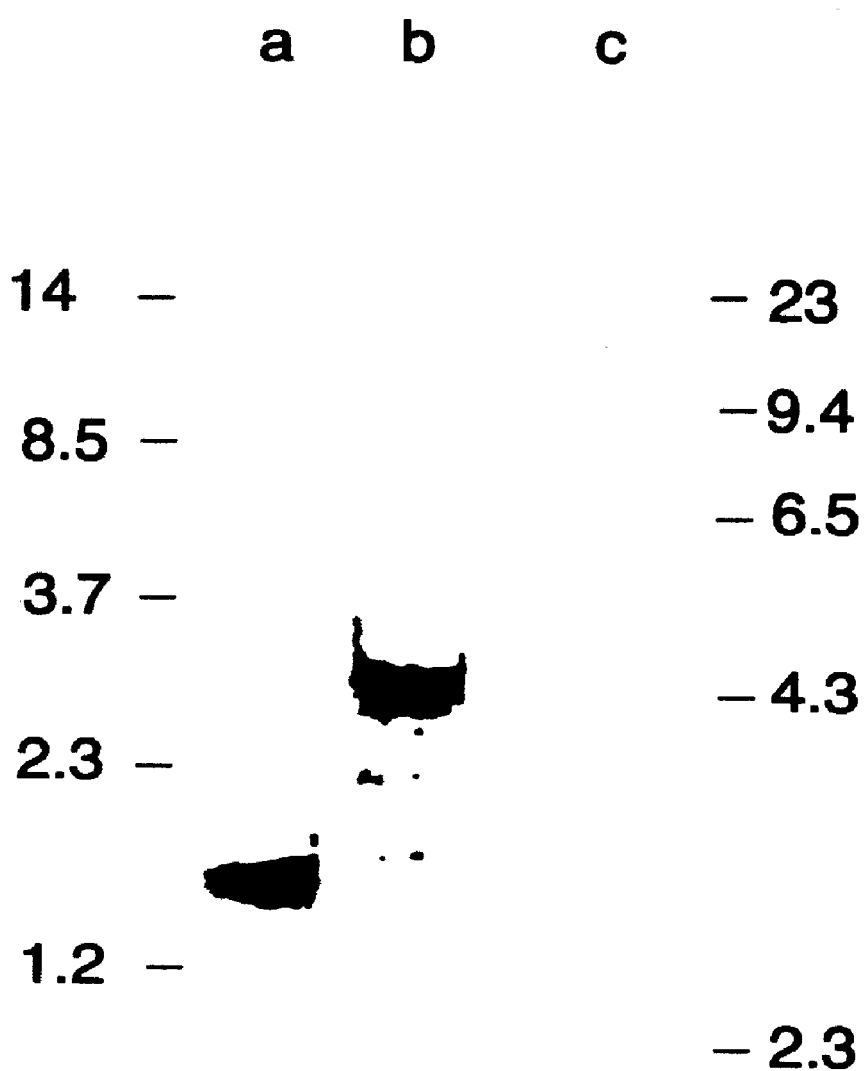

Restriction endonuclease treatment of guinea pig DNA (FIG. 8, lanes a&b) with analysis by Southern blotting under conditions of low stringency, revealed a single hybridizing band. Mouse genomic DNA cut with EcoRV (FIG. 8, lane c) also revealed a single hybridizing band. This data suggests that a single gene encodes guinea pig eotaxin and suggests the existence of a closely related gene in the mouse.

Figure 9:
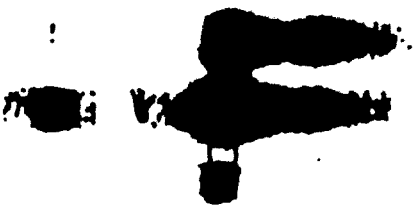

Eotaxin mRNA expression in different organs. Northern blot analyses of total RNA isolated from different guinea pig tissue samples revealed easily detectable constitutive expression of eotaxin in the lung (FIG. 9). The predominant hybridizing band had a size of ~0.8 kb. Other hybridizing bands were not detectable using poly A selected RNA. Lower levels were detectable in the intestines, stomach, heart, thymus, spleen, liver, testes, and kidney. In these latter tissues, eotaxin mRNA was more easily detected on poly A blots. The intestine showed some variability in expression between two different animals (FIG. 9). In addition, no RNA was detectable in the brain, bone marrow, or skin. Likewise, macrophages isolated and cultured from the spleen, a lung epithelial cell line, and a colon adenocarcinoma cell line were not found to express eotaxin mRNA. The finding of constitutive eotaxin mRNA in mucosal tissues wherein eosinophils predominantly reside (lung and intestines) suggests that eotaxin may play a role in the normal tissue homing and turnover of eosinophils.

D. The Induction of Eotaxin mRNA in Allergic Airway Inflammation

Figure 10:
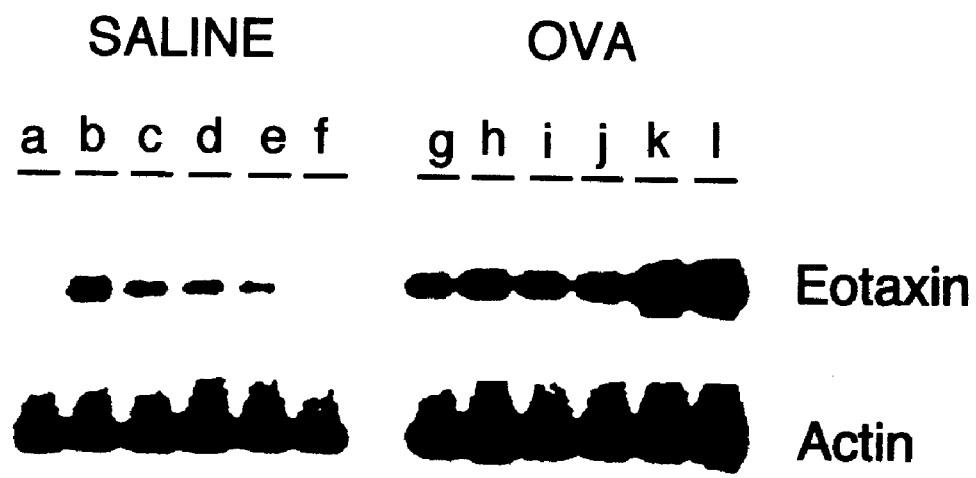
Figure 11:
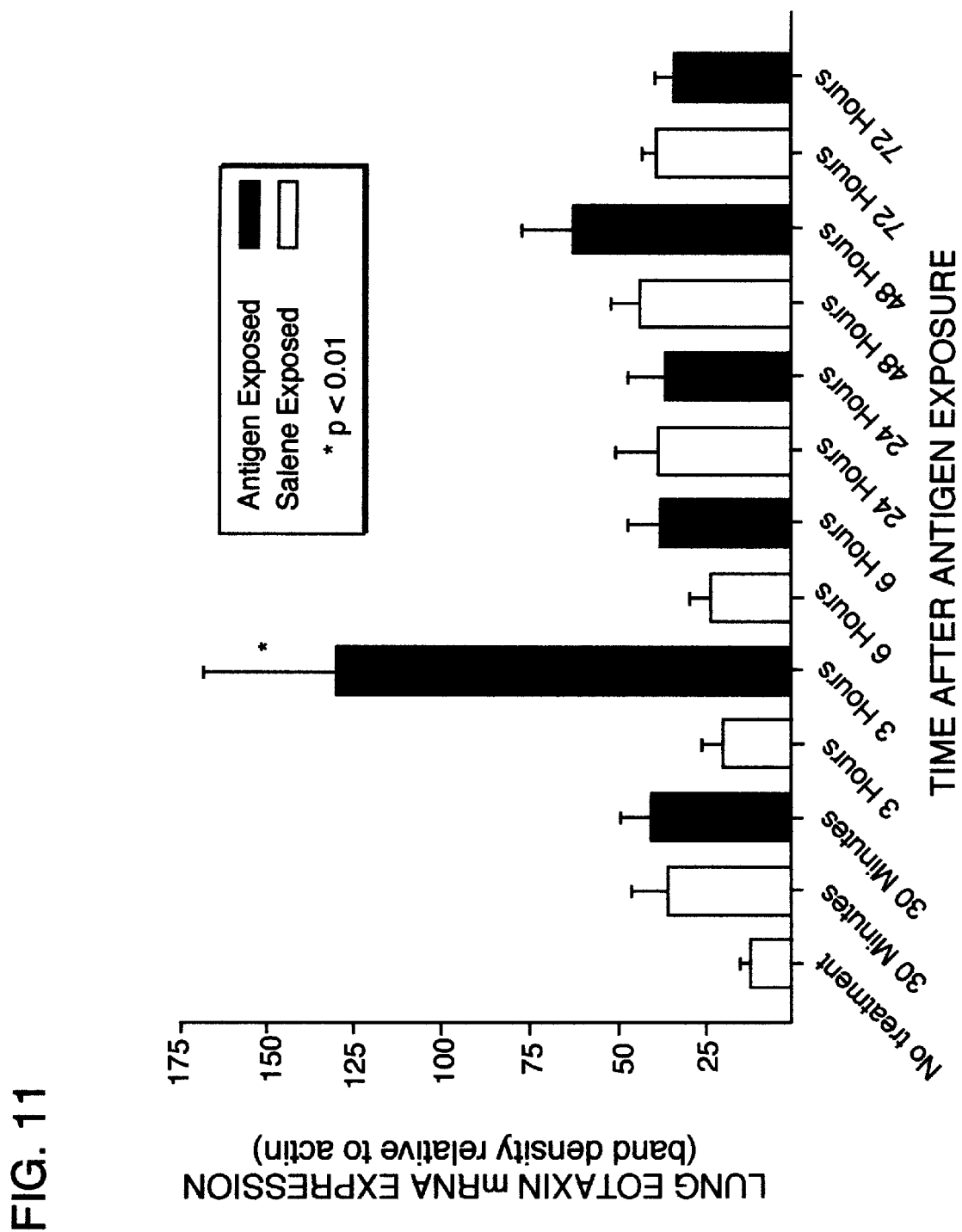

Since eotaxin mRNA was found to be expressed at relatively high levels in the lung of healthy guinea pigs, it was important to determine if this mRNA could account for all the protein released following allergen challenge, or whether eotaxin mRNA levels also increased. Therefore guinea pigs were sensitized to either aerosolized OVA or exposed to saline twice at a 7 day interval. Following a third dose of aerosolized antigen, the lungs of sensitized, but not saline exposed, guinea pigs develop a mucosal and submucosal eosinophil infiltration. The inflammation is most prominent at 17 hrs and persists for at least 3 days (Hutson, et al. (1988) Am. Rev. Respir. Dis. 137:548–57; Lilly, et al. (1994) J. Clin. Invest. 93:2667–2674). At various times after antigen challenge, poly A selected RNA were isolated from replicate lungs and equal amounts were examined by Northern blot analysis for eotaxin mRNA expression. Eotaxin mRNA levels increased ~6-fold ($p<0.01$) by 3 hrs compared with the lungs of saline treated guinea pigs (FIG. 10). All other time points were not significantly different (FIG. 11).

The cloning of guinea pig eotaxin cDNA has allowed us to make several observations relevant to the biology of eotaxin. The eotaxin gene is expressed at relatively high levels in the lungs of healthy guinea pigs without airway inflammation. In contrast, the chemotactic activity ascribed to eotaxin has been reported to be undetectable in the bronchoalveolar fluid of non-antigen challenged guinea pigs (Jose, et al. (1994) J. Exp. Med. 179:881–887). Thus, eotaxin mRNA is expressed at easily detectable constitutive levels in the lung when eotaxin activity is undetectable. This presents several alternative possibilities regarding the eotaxin protein: (1) it is rapidly degraded; (2) it is expressed at a low level which previously was not detectable; (3) it remains in an inaccessible location (e.g. a mast cell granule) and/or is biologically inhibited until after antigen challenge; (4) it requires additional biochemical processing for activation or some combination of the above. It is unlikely that eotaxin requires additional processing for activation since the cDNA structure predicts that active eotaxin is generated directly after removal of the leader sequence. It is interesting that the lungs of healthy guinea pigs without eosinophilic inflammation have detectable eosinophils in the bronchoalveolar fluid at baseline (Hutson, et al. (1988) Am. Rev. Respir. Dis. 137:548–57). Low levels of eotaxin protein may regulate basal eosinophil tissue homing.

Following antigen challenge, eotaxin gene expression in the lung is further increased during the early part of the late phase response. This change in mRNA parallels the peak changes in eotaxin protein release into the bronchoalveolar fluid which also peaks at 3 hours (Jose, et al. (1994) J. Exp. Med. 179:881–887). Only antigen exposure is associated with eosinophilic airway inflammation and bronchial hyperresponsiveness (Hutson, et al. (1988) 137:548–57; Sanjar, et al. (1990) J. Pharmacol. 99:679–86). Thus, up-regulation of gene expression, and not constitutive gene expression, is associated with the pathogenesis of airway disease. Eotaxin is likely to work in parallel with other cytokines generated during the late phase response. For example, IL-5, a cytokine produced during the late phase response, can prime eosinophils to respond to another C-C chemokine, RANTES, and can promote eosinophil tissue survival and activation (Rothenberg, et al. (1989) J. Immunol. 143:2311–6; Ebisawa et al. (1994) J. Immunol. 153: 2153–60).

Figure 14:
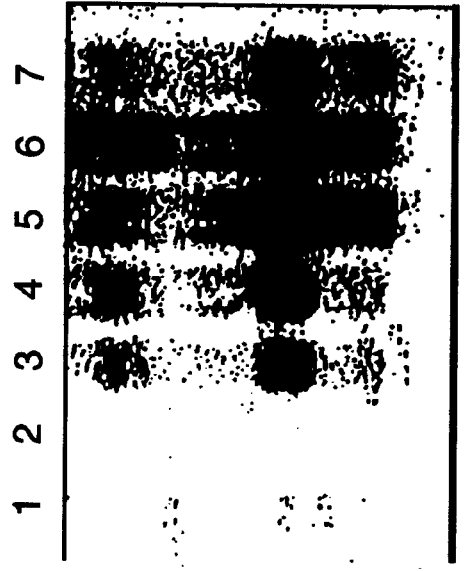
FIG. 14 shows expression of eotaxin in ulcerative colitis lesions (lanes 3–7). Lanes 1 and 2 are from normal colons.

Examination of RNA samples from multiple tissues for the expression of eotaxin mRNA reveals that in addition to the lung, lower levels are seen in a variety of other tissues. This suggests a more widespread function for this molecule. With the development of immunological reagents to detect the eotaxin protein, it will be important to compare protein and mRNA expression in these tissues. Finally, this cDNA enables the identification of analogous genes in other species and the development of molecular and immunological tools to examine the role of this molecule in allergic models and human disease. For example, FIG. 14 provides the human eotaxin sequence.

E. Eotaxin Genomic Structure and Chromosomal Localization

One way to clarify the question of whether guinea pig eotaxin is a homologue of a previously known chemokine is to shift the focus of attention to the mouse, in which a number of C-C chemokine genes are available for direct structural comparison. Accordingly, we used the coding region of guinea pig eotaxin cDNA and conditions of low stringency to screen a murine genomic library. Two overlapping clones were recovered and, from these, a 1.4 kb EcoRV genomic fragment was identified which hybridized to guinea pig eotaxin cDNA. Sequence analysis revealed that it encoded two exons with striking homology to guinea pig eotaxin (FIG. 1 and see below). Exon 1 mapped to the 5 kb EcoRI-XhoI fragment shown in FIG. 1 and a predicted signal peptide cleavage site was identified in the 50 region of exon 2 (FIG. 1) (Von Heijne, G. (1983) Eur. J. Biochem. 133, 17–21).

Figure 2A:
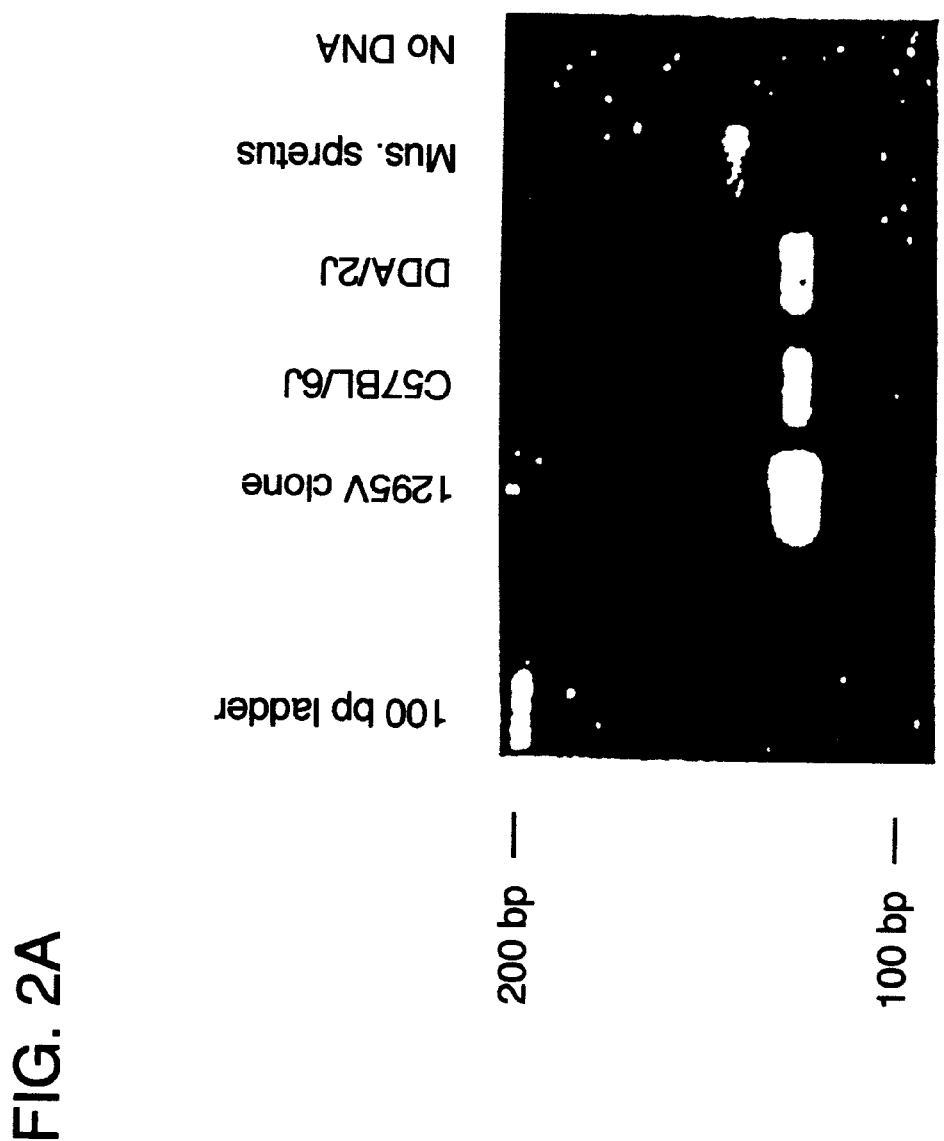
Figure 2B:
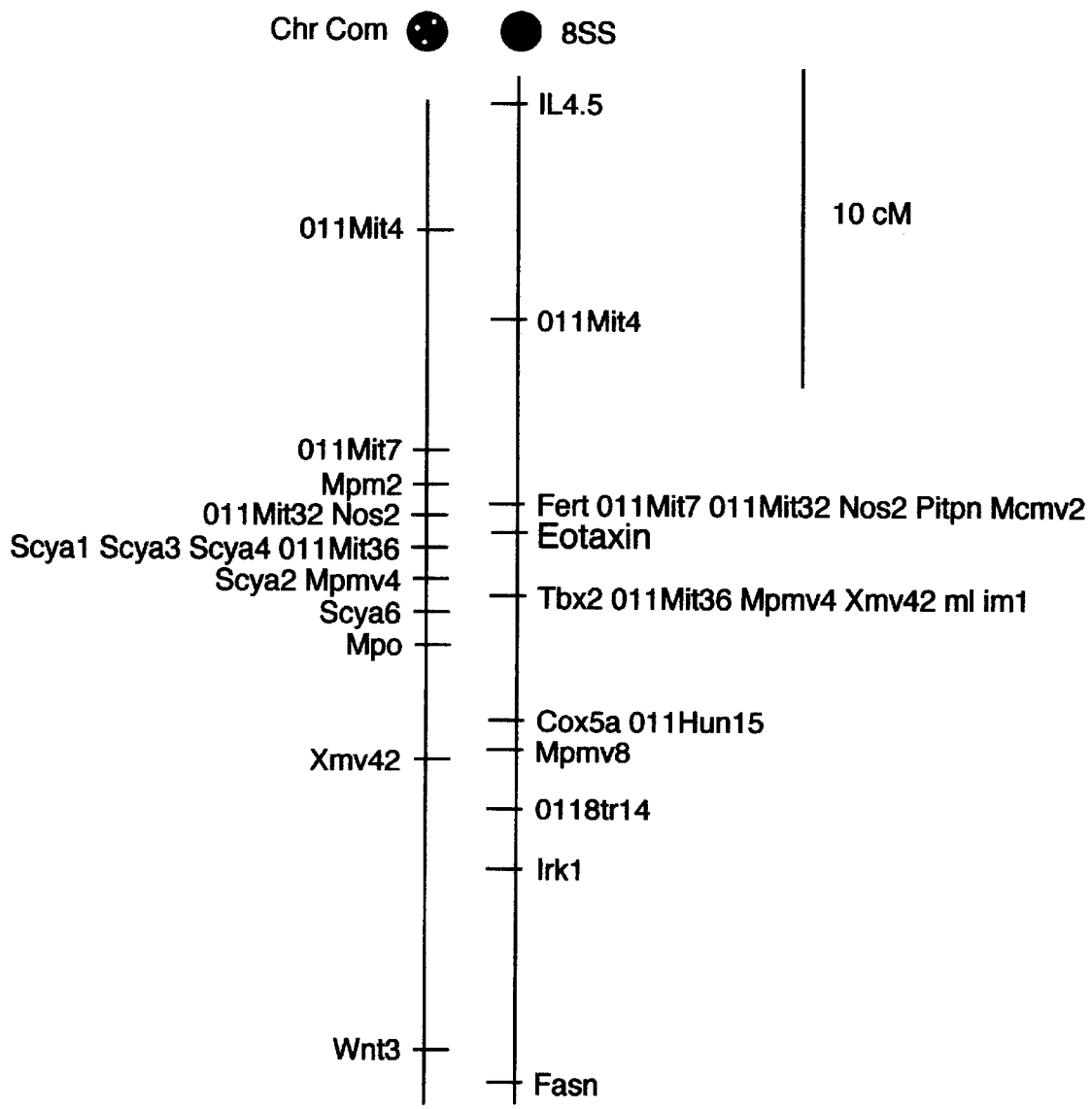

The sequence of the cloned genomic fragment revealed a stretch of 18 CA repeats in the intron between exons 2 and 3 that facilitated the chromosomal mapping of this gene. PCR primers flanking the repeat were used to amplify genomic DNA from several strains of mice and revealed a PCR product of similar size in the 129SV, DBA/2J, and C57BL/6J genomes. In contrast, DNA from Mus. spretus amplified a larger PCR product indicating a dinucleotide polymorphism (FIG. 2A). A panel of backcross DNA (F1× SPRET/Ei) was subsequently used to map the eotaxin gene based on this CA repeat polymorphism (Rowe, et al. (1994) Mamm. Gen. 5, 253–274). The eotaxin gene mapped to chromosome 11 between D11Mit markers 7 and 36 (FIG. 2B). A comparison to the consensus map from the Chromosome Committee (FIG. 2*b*) revealed this to be the C-C chemokine gene locus containing other chemokines (designated small inducible cytokines, Scy, a1–6, Lossie, et al. (1994) Mamm. Gen. 5, S164–180).

F. Analysis of Murine Eotaxin cDNA

In order to obtain the complete coding sequence to the candidate murine eotaxin gene, the 1.4 kb EcoRV genomic fragment containing exons 2 and 3 was used in a high stringency screen of a mouse lung cDNA library. Four positive plaques were identified, purified, and sequenced (FIG. 3A (SEQ ID NO: 5)). The cDNA from the longest cDNA was 994 bp long with an open reading frame that encoded 97 amino acids. A consensus sequence for translation initiation was identified around the first ATG codon in the longest open reading frame (Kozak, M. (1987) Nucl. Acids Res. 15, 8125–8148). The 5' region of the cDNA encoded a putative hydrophobic leader sequence whose cleavage site was predicted to occur between Ala and His (shown with the arrow in FIGS. 3A and 3B). These residues are conserved in guinea pig eotaxin. The 30 untranslated region contained three OAUUUAO domains (shown with hatched lines). Sequences of this type have been reported to decrease the mRNA stability of other cytokine mRNAs (Shaw, et al. (1986) Cell 46, 659–667) and are also present in guinea pig eotaxin (Rothenberg, et al. (1995) J. Exp. Med. 181, 1211–1216).

Examination of the nucleotide and protein sequences revealed that murine eotaxin was different than other sequenced murine chemokines and most homologous to guinea pig eotaxin (78% and 69% identical in bp and amino acids, respectively) (Table 1). Guinea pig and murine eotaxin are most homologous to members of the MCP family. Nonetheless, several features distinguish eotaxin from the MCP proteins (FIG. 3B (SEQ ID NOS. 7–14)). The predicted mature eotaxin proteins both start with His-Pro, whereas MCP family members start with Gln-Pro. Further, the third amino acid in mature guinea pig and murine eotaxin is Gly which distinguishes it from the MCPs. Guinea pig and murine eotaxin also have a gap at amino acids positions six and seven in their mature proteins which distinguish them from the other C-C chemokines (shown with *). As with all C-C chemokines, tyrosine28 is conserved in eotaxin (Lusti-Narasimhan, et al. (1995) J. Biol. Chem. 270, 2716–2721. Moreover, owing to the carboxy terminal end of eotaxin which is rich in basic amino acids (including the conservation of three consecutive Lys (shown with + symbol in FIG. 3B (SEQ ID NO: 7–14)), the predicted pI and charge at pH 7 is 10 and 12, respectively.

TABLE 1

Comparison of Mouse Eotaxin Coding cDNA with other Chemokines

| Chemokine | AA Similarity | AA Identity | BP Identity |
|---|---|---|---|
| gp Eotaxin* | 69% | 63% | 78% |
| mu MCP-1 | 64 | 49 | 63 |
| hu MCP-1 | 64 | 53 | 68 |
| gp MCP-1 | 60 | 45 | 60 |
| hu MCP-2* | 60 | 49 | ND |
| hu MCP-3* | 67 | 57 | 71 |
| mu MCP3(MARC) | 61 | 45 | 62 |
| hu MIP-1α* | 53 | 35 | 51 |
| hu MIP-1β | 51 | 34 | 52 |
| hu RANTES* | 49 | 32 | 46 |
| hu 1309 | 44 | 32 | 49 |
| mu TCA3 | 44 | 25 | 45 |
| hu IL-8* | 47 | 26 | 43 |

*Chemokines indicated have been shown to be active towards human eosinophils.
ND, not determined G. Eosinophil Chemotaxis by Murine Eotaxin Given the eosinophil chemoattractant activity of guinea pig eotaxin (Griffiths-Johnson, et al. (1993) Biochem. Biophys. Res. Comm. 197, 1167–1172; Jose, et al. (1994) J. Exp. Med. 179, 881–887), it was essential to test this property using the putative mouse homologue. Accordingly, the chemoattractant activity of the murine eotaxin protein was examined by expressing murine eotaxin cDNA in two different eukaryotic expression systems and testing their products on mouse eosinophils in-vitro. First, stable transfectants of plasmacytoma cells (J558L) with a MuLV MoLTR-eotaxin construct were derived and grown in serum free media. Second, the eotaxin cDNA was sub-cloned into the pcDNA-I/Amp plasmid and used for transient transfection of COS cells. The supernatants of these cells were used as a source of eotaxin protein.

Figure 4A:
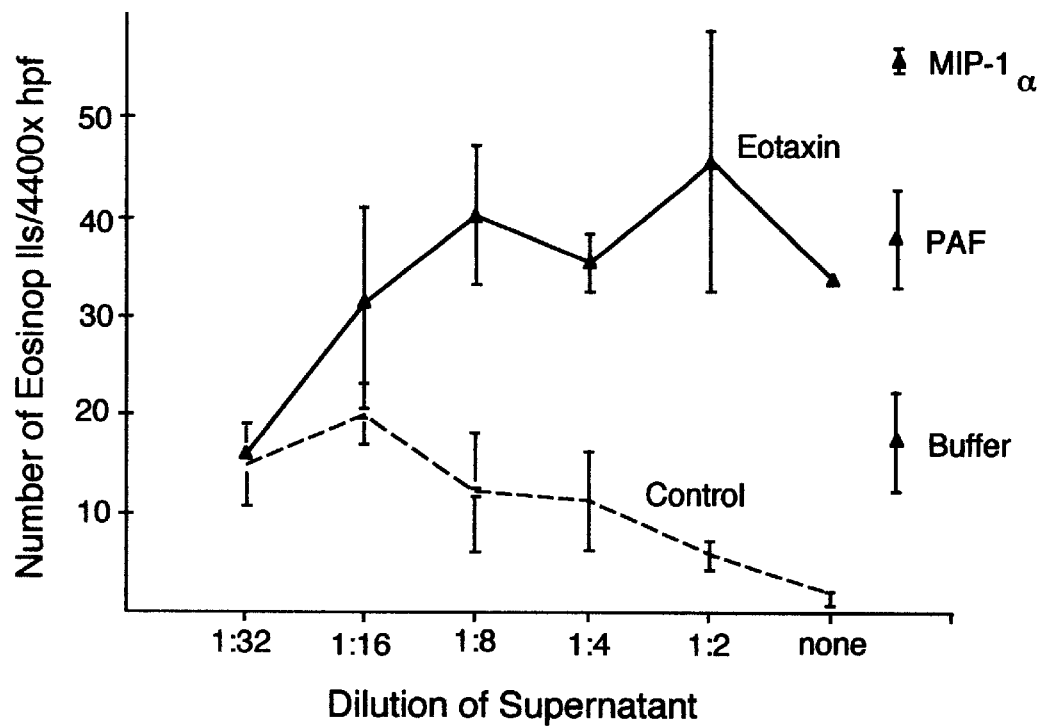
Figure 4B:
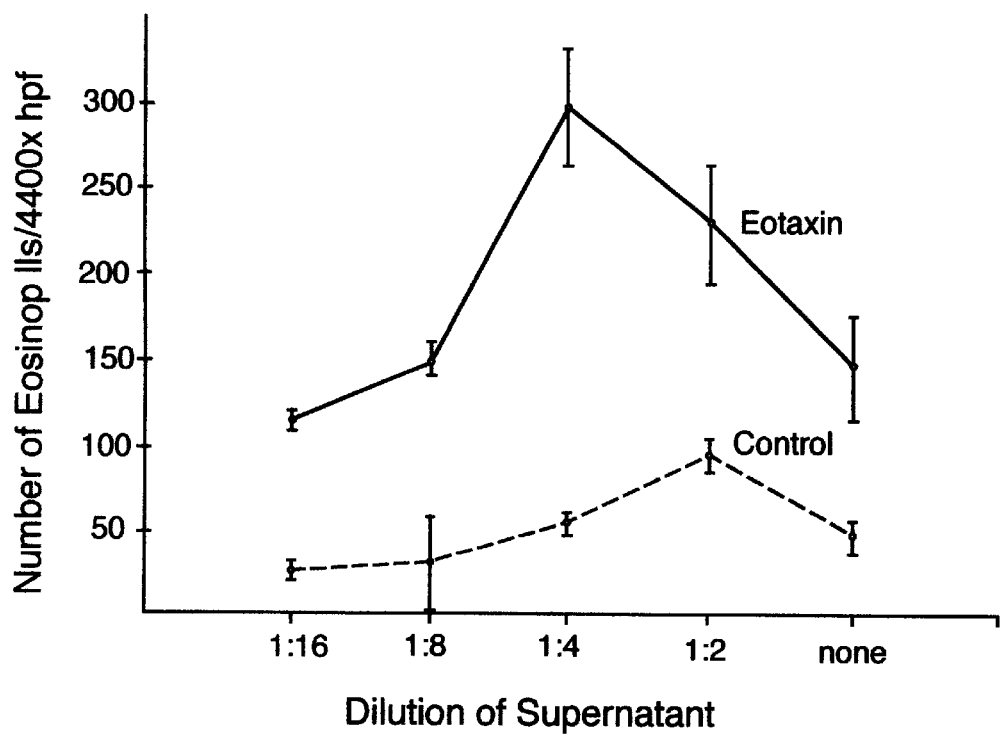

Normal mice do not have appreciable numbers of eosinophils so murine eosinophils were purified from IL-5 transgenic mice. IL-5 is an eosinophil growth and activating factor and IL-5 transgenic mice have profound eosinophilia that facilitates their isolation (Dent, et al. (1990) J. Exp. Med. 172, 1425–1431). Using a 48 well micro-chemotaxis chamber, murine eosinophils exhibited a strong chemotactic response to 10-6-10-7 M PAF and 100–1000 ng/ml of recombinant murine MIP-la, both positive controls (FIG. 4A). The eotaxin J558L supernatant also demonstrated a strong eosinophil chemotactic activity compared to the negative control supernatant (FIG. 4B). The possible inhibitory effect of the control supernatant may relate to the release of toxic metabolites during the harvesting of the cell supernatant. The supernatant from transfected COS cells also produced an increase in chemotaxis compared to mock-transfected COS cell supernatant (FIG. 4B). The larger chemotactic response in FIG. 4B compared with FIG. 4A is likely due to the presence of FCS in the COS cell supernatants. In all experiments, migrating cells were >95% eosinophils. Eotaxin-COS cell and J558L cell supernatants had no activity on mouse macrophages or neutrophils whereas the macrophages had a strong chemotactic response to murine MIP-1a and the neutrophils had a strong chemotactic response to KC.

H. Analysis of Eotaxin mRNA Expression in Mice

Figure 5:
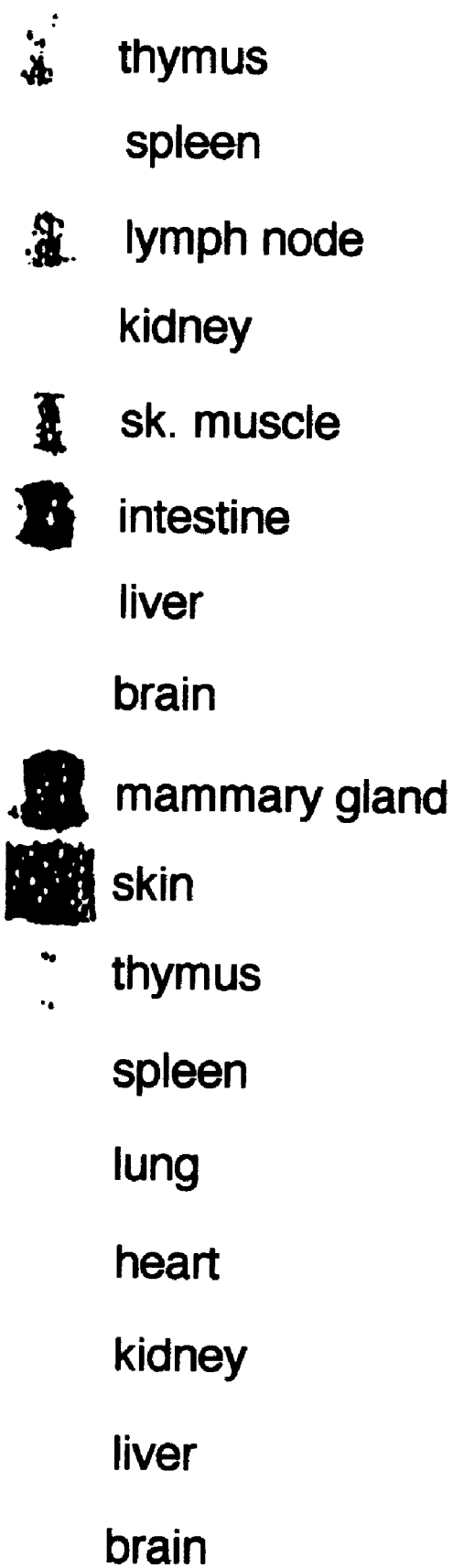

Because information about function can be inferred from the expression pattern of a gene, eotaxin mRNA was assessed in various organs of normal mice. Analysis of an equal amount of total RNA by optical density and ethidium bromide staining, revealed easily detectable levels of eotaxin mRNA expression in skin, thymus, lymph node, mammary gland, skeletal muscle, and lower levels in the heart and lung (FIG. 5). Other tissue with expression included the stomach, tongue, and one spleen sample (data not shown). This relative expression pattern varied somewhat between RNA preparations, probably reflecting strain and age variability in the mice. As predicted from the size of the cDNA, the mRNA transcript was approximately 1 kb.

I. Regulation of Eotaxin mRNA Expression in Mice

Figure 6A:
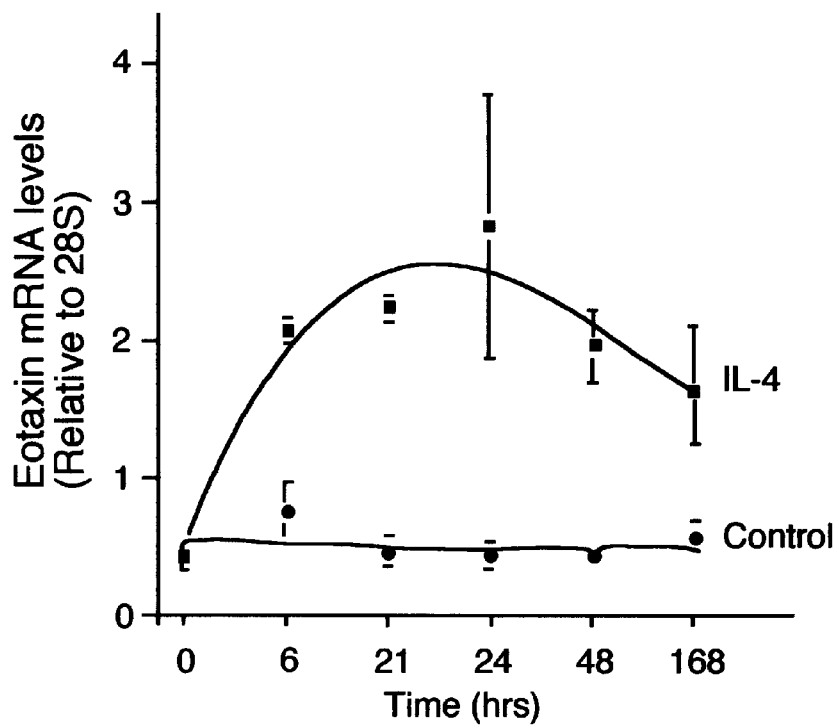
Figure 6B:
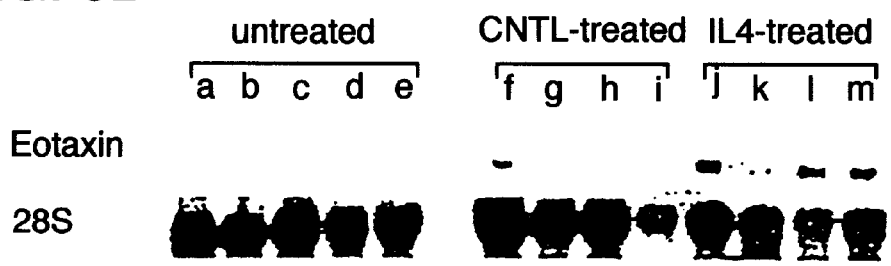

When IL-4 transfected tumor cells are transplanted into the skin of syngeneic or immunodeficient mice, there is a remarkable eosinophil infiltration within 18 hours (Tepper, et al. (1989) Cell 57, 503–512). These eosinophils have been shown to be critical for the anti-tumor effect of IL-4, though the mechanism of their recruitment is not understood. Eotaxin would be a logical candidate for this role. To assess this possibility, eotaxin mRNA expression at the site of tumor cell transplantation was assayed at various times after transplantation of the IL-4-producing tumor cells. Within six hours, there was a marked increase in eotaxin mRNA compared with controls which consisted of transplanting untransfected tumor calls or untreated skin (FIG. 6A). This increase persisted for 7 days. FIG. 6B shows representative data at the 24 hour time point for eotaxin mRNA in the skin of untransplanted mice and mice transplanted with IL-4-producing and non-producing tumor cells.

J. Production of Eotaxin by Endothelial Cells

Since endothelial cells are known to produce several chemokines including MCP-1 (Rollins, B. J. & Pober, J. S. (1991) Am. J. Path. 138, 1315–1319) that are increased by interferon-∂ (IFN-∂), the ability of IFN-∂ to induce eotaxin mRNA expression in endothelial cells was also examined. An SV40 immortalized murine endothelial cell line was treated with cytokine and total RNA was analyzed by RNA blot hybridization.

Eotaxin mRNA was undetectable in non-treated cells, but was detectable by 6 hrs of treatment with IFN-∂ (FIG. 6c) and returned to an undetectable level by 18 hrs. As a control, murine macrophage chemoattractant protein-1 (MCP-1) mRNA was found to be readily detectable constitutively and to be increased by IFN-∂ treatment (FIG. 6c) as previously reported (36). Eotaxin mRNA expression in mast cells and macrophages was also examined. Whereas the macrophage cell line, RAW 267.4, had easily detectable levels of murine MCP-1 mRNA which increased after 18 hrs of IFN-∂, both untreated and treated cells had no eotaxin mRNA detectable (data not shown). Similarly, a mouse mast cell line (P815) and Con-A activated mouse bone marrow derived mast cells had easily detectable expression of MCP-1 mRNA, but no detectable expression of eotaxin mRNA (data not shown).

K. Cloning of Human Eotaxin

Human eotaxin was cloned by screening a human genomic library (λ placental library) with a mouse eotaxin probe generated by PCR using mouse coding sequences. mcp-1 sequences were eliminated by screening the library at high stringency and eliminating those clones that hybridized with mcp-1 sequences at high stringency. The human sequence is shown in FIG. 12A (SEQ ID NO: 17), FIG. 12B (SEQ ID NO: 19), and FIG. 12C (SEQ ID NO: 21).

L. Human Eotaxin is Expressed in Ulcerative Colitis Lesions, but not in Tissue from Normal Colon FIG. 13 shows that the human eotaxin RNA is expressed at detectable levels in all five of the tissues tested from ulcerative colitis lesions. By contrast, no eotaxin expression was detected in the colon tissue form unaffected individuals. This is consistent with a causative role for eotaxin in the pathology of ulcerative colitis.

Sequence Deposits

The murine sequence data reported herein has been deposited in the GenBank data base (accession no. U26426) and the chromosomal mapping data has been deposited in the Mouse Genome Data Base (accession no. MGD-CREX-329).

Other Embodiments

In other embodiments, the invention includes any protein which is substantially identical to an eotaxin polypeptide FIGS. 3A (SEQ ID NO:6), FIG. 7 (SEQ ID NO:16), and 12A (SEQ ID NO:18), 12B (SEQ ID NO:20), and 12C (SEQ ID NO:22) preferably the sequence of FIG. 3A (SEQ ID NO:6) or FIG. 12A, 12B, and 12C (SEQ ID NOS: 18, 20, and 22); such homologs include other substantially pure naturally occurring mammalian eotaxin proteins as well as allelic variations; natural mutants; induced mutants; proteins encoded by DNA that hybridizes to the eotaxin sequences of FIGS. 3A (SEQ ID NO: 5), FIG. 7 (SEQ ID NO: 15), and 12A (SEQ ID NO: 17), 12B (SEQ ID NO: 19), and 12C (SEQ ID NO: 21) (preferably the sequence of FIG. 3A (SEQ ID NO: 5) or FIG. 12A, 12B, and 12C (SEQ ID NOS: 17, 19, and 21) under high stringency conditions or low stringency conditions (e.g., washing at 2×SSC at 40° C. with a probe length of at least 40 nucleotides); and polypeptides or proteins specifically bound by antisera directed to a eotaxin polypeptide. The term also includes chimeric polypeptides that include an eotaxin fragment.

The invention further includes analogs of the eotaxin polypeptide. Analogs can differ from the naturally occurring eotaxin protein by amino acid sequence differences, by post-translational modifications, or by both. Analogs of the invention will generally exhibit at least 70%, more preferably 80%, even more preferably 90%, and most preferably 95% or even 99%, identity with all or part of a naturally occurring eotaxin sequence. The length of comparison sequences will be at least 8 amino acid residues, preferably at least 24 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally occurring eotaxin polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, hereby incorporated by reference; or Ausubel et al., supra, hereby incorporated by reference). Also included are cyclized peptides molecules and analogs which contain residues other than L-amino acids, e.g., D-amino acids or non-naturally occurring or synthetic amino acids, e.g., β or γ amino acids.

In addition to full-length polypeptides, the invention also includes eotaxin polypeptide fragments. As used herein, the term "fragment" means at least 10 contiguous amino acids, preferably at least 30 contiguous amino acids, more preferably at least 50 contiguous amino acids, and most preferably at least 60 to 80 or more contiguous amino acids. Fragments of eotaxin can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which exhibit biological activity (for example, the ability to act as an eosinophil chemoattractant as described herein). Preferably, an eotaxin polypeptide, fragment, or analog exhibits at least 10%, more preferably 30%, and most preferably, 70% or more of the biological activity of a full length naturally occurring human murine eotaxin polypeptide.

What is claimed is:

1. Substantially pure DNA encoding the amino acid sequence of SEQ ID NO: 6.
2. Substantially pure DNA encoding the amino acid sequence of SEQ ID NO: 16.
3. Substantially pure DNA encoding the amino acid sequence of SEQ ID NO:27.
4. A purified DNA having the nucleotide sequence shown in SEQ ID NO: 5.
5. A purified DNA having the nucleotide sequence shown in SEQ ID NO:15.
6. A purified DNA having the nucleotide sequence shown in SEQ ID NO:26.
7. The DNA of any one of claims 1, 2, 3, 4, 5, or 6, wherein said nucleic acid is cDNA.
8. A vector comprising the DNA of any one of claims 1, 2, 3, 4, 5, 6, said vector being capable of directing expression of the peptide encoded by said DNA in a vector-containing cell.
9. Substantially pure nucleic acid encoding the murine eotaxin polypeptide of SEQ ID NO: 6.
10. Substantially pure nucleic acid encoding the guinea pig eotaxin polypeptide of SEQ ID NO: 16.
11. Substantially pure nucleic acid encoding the human eotaxin polypeptide of SEQ ID NO: 27.

* * * * *

UNITED STATES PATENT AND TRADEMARK OFFICE
CERTIFICATE OF CORRECTION

PATENT NO.   : 6,403,782 B1
DATED        : June 11, 2002
INVENTOR(S)  : Luster et al.

It is certified that error appears in the above-identified patent and that said Letters Patent is hereby corrected as shown below:

Title page,
Item [56], References Cited, OTHER PUBLICATIONS, Mikayama et al., delete "vol" and replace with -- Vol. --;

Column 2,
Line 33, delete "(SEQ ID NOS. 7-14(c)" and replace with
-- (SEQ ID NOS. 7-14);(c) --;

Column 3,
Line 1, delete "Eotaxin" and replace with -- eotaxin --;
Line 66, delete "FIGS 13 SEQ" and replace with -- FIGS 13 (SEQ --;

Column 4,
Line 27, insert missing sentence after NO:22 to read: -- Preferably, the identity is to the sequence in either FIG. 12 --;

Column 5,
Line 22, delete "Eotaxin" and replace with -- eotaxin --;

Column 6,
Line 55, delete "substitutions, deletions, substitutions, and other modifications" and replace with -- substitutions, deletions, and other modifications --;
Line 57, delete "glycine alanine;" and replace with -- glycine, alanine; --;

Column 7,
Line 6, delete "encoding an the peptide;" and replace with -- encoding the peptide; --;

Column 8,
Line 10, delete "$^=$P or $^±$S" and replace with -- $^{32}$P or $^{35}$S) --;

Column 9,
Lines 34-35, delete "lanes f-i" and replace with -- (lanes f-i) --;

Column 10,
Line 18, delete "SEID NO:26)" and replace with -- (SEQ ID NO: 26) --;

Column 11,
Lines 7-8, delete "Dent, et al. Id.)." and replace with -- (Dent, et al., Id.). --;

Column 15,
Line 16, delete "factor-a" and replace with -- factor-X --;

UNITED STATES PATENT AND TRADEMARK OFFICE
CERTIFICATE OF CORRECTION

PATENT NO. : 6,403,782 B1
DATED : June 11, 2002
INVENTOR(S) : Luster et al.

Figure 6C:
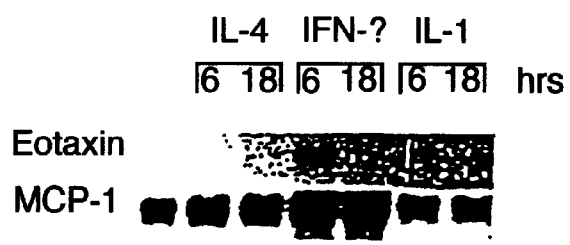

It is certified that error appears in the above-identified patent and that said Letters Patent is hereby corrected as shown below:

Column 16,
Line 27, delete "sample eotaxin-specific" and replace with -- sample.Eotaxin-specific --;

Column 18,
Line 34, delete "370º" and replace with -- 37º --;
Line 34, delete "or 60s" and replace with -- for 60s --;

Column 21,
Lines 15-16, delete "Macrophages cells" to -- Macrophage cells --;

Column 24,
Line 49, italicize "Mus. Spretus";

Column 25,
Line 52, Table 1, delete "hu1309" and replace with -- huI309 --;

Column 26,
Line 46, delete "I. Regulation of Eotaxin mRNA Expression in Mice" and replace with
-- I.Regulation of Eotaxin mRNA Expression In-Vivo by IL-4 --;

Column 27,
Line 7, delete "FIG. 6c" and replace with -- FIG.6c --;
Line 11, delete "FIG. 6c" and replace with -- FIG.6 --;
Line 35, delete "form" and replace with -- from --;
Lines 49-50, delete "preferably" and replace with -- (preferably --;
Lines 49-50, delete "and 22);" and replace with -- and 22)) --;

UNITED STATES PATENT AND TRADEMARK OFFICE
CERTIFICATE OF CORRECTION

PATENT NO. : 6,403,782 B1
DATED : June 11, 2002
INVENTOR(S) : Luster et al.

It is certified that error appears in the above-identified patent and that said Letters Patent is hereby corrected as shown below:

Column 28,
Line 3, delete "and 21)" and replace with -- and 21)) --;
Line 33, delete "cyclized peptides molecules and analogs" and replace with -- cyclized peptides, molecules, and analogs --.

Signed and Sealed this

Thirty-first Day of December, 2002

JAMES E. ROGAN
*Director of the United States Patent and Trademark Office*

SEQUENCE LISTING

<160> NUMBER OF SEQ ID NOS: 27

<210> SEQ ID NO 1
<211> LENGTH: 21
<212> TYPE: DNA

```
<213> ORGANISM: Artificial Sequence
<220> FEATURE:
<221> NAME/KEY: misc_feature
<222> LOCATION: (1)...(21)
<223> OTHER INFORMATION: n = A,T,C or G
<223> OTHER INFORMATION: Synthetic

<400> SEQUENCE: 1
ccggaattcc ayccnggnat h                                         21

<210> SEQ ID NO 2
<211> LENGTH: 26
<212> TYPE: DNA
<213> ORGANISM: Artificial Sequence
<220> FEATURE:
<223> OTHER INFORMATION: Synthetic

<400> SEQUENCE: 2
cgcggatccg crcadatcat yttrtc                                    26

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
caccctgaaa gccatagtgt                                           20

<210> SEQ ID NO 4
<211> LENGTH: 19
<212> TYPE: DNA
<213> ORGANISM: Mus musculus

<400> SEQUENCE: 4
tgtgtacctg ggaaattag                                            19

<210> SEQ ID NO 5
<211> LENGTH: 994
<212> TYPE: DNA
<213> ORGANISM: Mus musculus
<220> FEATURE:
<221> NAME/KEY: CDS
<222> LOCATION: (35)...(325)

<400> SEQUENCE: 5
cccgggcagt aacttccatc tgtctccctc cacc atg cag agc tcc aca gcg ctt      55
                                     Met Gln Ser Ser Thr Ala Leu
                                       1               5 cta ttc ctg ctg ctc acg gtc act tcc ttc a cc tcc cag gtg ctg gct     103
Leu Phe Leu Leu Leu Thr Val Thr Ser Phe T hr Ser Gln Val Leu Ala
         10                  15                  20 cac cca ggc tcc atc cca act tcc tgc tgc t tt atc atg acc agt aag     151
His Pro Gly Ser Ile Pro Thr Ser Cys Cys P he Ile Met Thr Ser Lys
     25                  30                  35 aag atc ccc aac aca cta ctg aag agc tac a aa aga atc acc aac aac     199
Lys Ile Pro Asn Thr Leu Leu Lys Ser Tyr L ys Arg Ile Thr Asn Asn
 40                  45                  50                  55 aga tgc acc ctg aaa gcc ata gtc ttc aag a cc agg ttg ggc aaa gag     247
Arg Cys Thr Leu Lys Ala Ile Val Phe Lys T hr Arg Leu Gly Lys Glu
                 60                  65                  70 atc tgt gct gac ccc aag aag aag tgg gtc c ag gat gcc aca aag cac     295
Ile Cys Ala Asp Pro Lys Lys Lys Trp Val G ln Asp Ala Thr Lys His
             75                  80                  85
```

-continued

```
ctg gac caa aaa ctc caa act cca aaa cca t aaacaacct cctctcttga       345
Leu Asp Gln Lys Leu Gln Thr Pro Lys Pro
        90                  95 cactaaccca gagcctaaga actgcttgat tccttctctt tcctaagacg t gctctgagg   405 gaatatcagc accagtcgcc caaggacttg gcttcatgta gttccagatg g gactggaag   465 tcattatctt tgctgaaata agtcagactc aaaagattgt gtaatttctt g catatgcaa   525 catcttaaaa gggggcatg aaaggagatg tgggattatt gaggaacaca a tgggacgag    585 ttaggactaa ctgacgataa tagcagctta tacacatata tgaaaatgtc t attgttttg   645 cacaattaat atacactaat taaaattaat ttacactaac taaatgttaa tatttaaag    705 acatgttaca tttaagaaat tggagtttta aagcataatt taatggatat c agtccttt    765 tgttattgtg ttctttgttt gcttgcttgt ttgaaacagg gactcactgt a tcaccctga   825 ctgacctgta actcactgtg tagaccaggc tgacctcaaa ctcacagaaa t ttacctgcc   885 tctgccttta aagtgctacc atgccaagcc agaatgtttt ttattagaat a taccaatta   945 tatataataa aatattttac tacaaaaaaa aaaaaaaaa aaaaaaaa               994
```

<210> SEQ ID NO 6
<211> LENGTH: 97
<212> TYPE: PRT
<213> ORGANISM: Mus musculus

<400> SEQUENCE: 6

```
Met Gln Ser Ser Thr Ala Leu Leu Phe Leu L eu Leu Thr Val Thr Ser
1               5                   10                  15

Phe Thr Ser Gln Val Leu Ala His Pro Gly S er Ile Pro Thr Ser Cys
                20                  25                  30

Cys Phe Ile Met Thr Ser Lys Lys Ile Pro A sn Thr Leu Leu Lys Ser
            35                  40                  45

Tyr Lys Arg Ile Thr Asn Asn Arg Cys Thr L eu Lys Ala Ile Val Phe
        50                  55                  60

Lys Thr Arg Leu Gly Lys Glu Ile Cys Ala A sp Pro Lys Lys Lys Trp
65                  70                  75                  80

Val Gln Asp Ala Thr Lys His Leu Asp Gln L ys Leu Gln Thr Pro Lys
                85                  90                  95

Pro
```

<210> SEQ ID NO 7
<211> LENGTH: 98
<212> TYPE: PRT
<213> ORGANISM: Homo sapiens

<400> SEQUENCE: 7

```
Met Gln Ser Ser Thr Ala Leu Leu Phe Leu L eu Leu Thr Val Thr Ser
1               5                   10                  15

Phe Thr Ser Gln Val Leu Ala His Pro Pro G ly Ser Ile Pro Thr Ser
                20                  25                  30

Cys Cys Phe Ile Met Thr Ser Lys Lys Ile P ro Asn Thr Leu Leu Lys
            35                  40                  45

Ser Tyr Lys Arg Ile Thr Asn Asn Arg Cys T hr Leu Lys Ala Ile Val
        50                  55                  60

Phe Lys Thr Arg Leu Gly Lys Glu Ile Cys A la Asp Pro Lys Lys Lys
65                  70                  75                  80

Trp Val Gln Asp Ala Thr Lys His Leu Asp G ln Lys Leu Gln Thr Pro
```

-continued

```
                   85                   90                   95

Lys Pro

<210> SEQ ID NO 8
<211> LENGTH: 96
<212> TYPE: PRT
<213> ORGANISM: Guinea pig

<400> SEQUENCE: 8

Met Lys Val Ser Thr Ala Phe Leu Cys Leu Leu Leu Thr Val Ser Ala
1               5                   10                  15

Phe Ser Ala Gln Val Leu Ala His Pro Gly Ile Pro Ser Ala Cys Cys
            20                  25                  30

Phe Arg Val Thr Asn Lys Lys Ile Ser Phe Gln Arg Leu Lys Ser Tyr
        35                  40                  45

Lys Ile Ile Thr Ser Ser Lys Cys Pro Gln Thr Ala Ile Val Phe Glu
    50                  55                  60

Ile Lys Pro Asp Lys Met Ile Cys Ala Asp Pro Lys Lys Lys Trp Val
65                  70                  75                  80

Gln Asp Ala Lys Lys Tyr Leu Asp Gln Ile Ser Gln Thr Thr Lys Pro
                85                  90                  95

<210> SEQ ID NO 9
<211> LENGTH: 96
<212> TYPE: PRT
<213> ORGANISM: Guinea pig

<400> SEQUENCE: 9

Met Gln Arg Ser Ser Val Leu Leu Cys Leu Leu Val Ile Glu Ala Thr
1               5                   10                  15

Phe Cys Ser Leu Leu Met Ala Gln Pro Asp Gly Val Asn Thr Pro Thr
            20                  25                  30

Cys Cys Tyr Thr Phe Asn Lys Gln Ile Pro Leu Lys Arg Lys Gly Tyr
        35                  40                  45

Glu Arg Ile Thr Ser Ser Arg Cys Pro Gln Glu Ala Val Ile Phe Arg
    50                  55                  60

Thr Leu Lys Asn Lys Glu Val Cys Ala Asp Pro Thr Gln Leu Trp Val
65                  70                  75                  80

Gln Asp Tyr Ile Ala Lys Leu Asp Gln Arg Thr Gln Gln Lys Gln Asn
                85                  90                  95

<210> SEQ ID NO 10
<211> LENGTH: 99
<212> TYPE: PRT
<213> ORGANISM: Homo sapiens

<400> SEQUENCE: 10

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80
```

```
Lys Trp Val Gln Asp Ser Met Asp His Leu Asp Lys Gln Thr Gln Thr
                85                  90                  95

Pro Lys Thr

<210> SEQ ID NO 11
<211> LENGTH: 99
<212> TYPE: PRT
<213> ORGANISM: Homo sapiens

<400> SEQUENCE: 11

Met Gln Val Pro Val Met Leu Leu Gly Leu Leu Phe Thr Val Ala Gly
  1               5                  10                  15

Trp Ser Ile His Val Leu Ala Gln Pro Asp Ala Val Asn Ala Pro Leu
                 20                  25                  30

Thr Cys Cys Tyr Ser Phe Thr Ser Lys Met Ile Pro Met Ser Arg Leu
                 35                  40                  45

Glu Ser Tyr Lys Arg Ile Thr Ser Ser Arg Cys Pro Lys Glu Ala Val
             50                  55                  60

Val Phe Val Thr Lys Leu Lys Arg Glu Val Cys Ala Asp Pro Lys Lys
 65                  70                  75                  80

Glu Trp Val Gln Thr Tyr Ile Lys Asn Leu Asp Arg Asn Gln Met Arg
                85                  90                  95

Ser Glu Pro

<210> SEQ ID NO 12
<211> LENGTH: 77
<212> TYPE: PRT
<213> ORGANISM: Homo sapiens

<400> SEQUENCE: 12

Ala Gln Pro Asp Ser Val Ser Ile Pro Ile Thr Cys Cys Phe Asn Val
  1               5                  10                  15

Ile Asn Arg Lys Ile Pro Ile Gln Arg Leu Glu Ser Tyr Thr Arg Ile
                 20                  25                  30

Thr Asn Ile Gln Cys Pro Lys Glu Ala Val Ile Phe Lys Thr Lys Arg
                 35                  40                  45

Gly Lys Glu Val Cys Ala Asp Pro Lys Glu Arg Trp Val Arg Asp Ser
             50                  55                  60

Met Lys His Leu Asp Gln Ile Phe Gln Asn Leu Lys Pro
 65                  70                  75

<210> SEQ ID NO 13
<211> LENGTH: 110
<212> TYPE: PRT
<213> ORGANISM: Homo sapiens

<400> SEQUENCE: 13

Met Trp Lys Pro Met Pro Ser Pro Ser Asn Met Lys Ala Ser Ala
  1               5                  10                  15

Ala Leu Leu Cys Leu Leu Leu Thr Ala Ala Ala Phe Ser Pro Gln Gly
                 20                  25                  30

Leu Ala Gln Pro Val Gly Ile Asn Thr Ser Thr Thr Cys Cys Tyr Arg
                 35                  40                  45

Phe Ile Asn Lys Lys Ile Pro Lys Gln Arg Leu Glu Ser Tyr Arg Arg
             50                  55                  60

Thr Thr Ser Ser His Cys Pro Arg Glu Ala Val Ile Phe Lys Thr Lys
 65                  70                  75                  80
```

```
Leu Asp Lys Glu Ile Cys Ala Asp Pro Thr G ln Lys Trp Val Gln Asp
                85                  90                  95

Phe Met Lys His Leu Asp Lys Lys Thr Gln T hr Pro Lys Leu
            100                 105             110

<210> SEQ ID NO 14
<211> LENGTH: 92
<212> TYPE: PRT
<213> ORGANISM: Homo sapiens

<400> SEQUENCE: 14

Met Arg Ile Ser Ala Thr Leu Leu Cys Leu L eu Leu Ile Ala Ala Ala
 1               5                  10                  15

Phe Ser Ile Gln Val Trp Ala Gln Pro Asp G ly Pro Asn Ala Ser Thr
            20                  25                  30

Cys Cys Tyr Val Lys Lys Gln Lys Ile Pro L ys Arg Asn Leu Lys Ser
            35                  40                  45

Tyr Arg Arg Ile Thr Ser Ser Arg Cys Pro T rp Glu Ala Val Ile Phe
        50                  55                  60

Lys Thr Lys Lys Gly Met Glu Val Cys Arg G lu Ala His Gln Lys Trp
65                  70                  75                  80

Val Glu Glu Ala Ile Ala Tyr Leu Asp Met L ys Thr
                85                  90
```

```
<210> SEQ ID NO 15
<211> LENGTH: 818
<212> TYPE: DNA
<213> ORGANISM: Guinea pig
<220> FEATURE:
<221> NAME/KEY: CDS
<222> LOCATION: (69)...(356)

<400> SEQUENCE: 15
ctcgtgccgc tcgtgccgga acaacccaga aactattgtc acgctgcaac c catctgcac      60 actgcacc atg aaa gtc tcc aca gcg ttt ctg tgc  ctg ctg ctc aca gtc     110
         Met Lys Val Ser Thr Ala Phe Leu Cys  Leu Leu Leu Thr Val
          1               5                   10 tct gct ttc agc gcc cag gtg ctc gcc cat c ca ggt atc cca agt gcc     158
Ser Ala Phe Ser Ala Gln Val Leu Ala His P ro Gly Ile Pro Ser Ala
 15              20                  25                  30 tgc tgc ttt cgt gtg acc aat aag aag atc t cc ttt cag cga ctg aag     206
Cys Cys Phe Arg Val Thr Asn Lys Lys Ile S er Phe Gln Arg Leu Lys
            35                  40                  45 agc tac aaa ata atc acc agc agc aaa tgt c cc cag aca gcc att gtc     254
Ser Tyr Lys Ile Ile Thr Ser Ser Lys Cys P ro Gln Thr Ala Ile Val
        50                  55                  60 ttt gag atc aaa cct gac aaa atg ata tgt g cg gac ccc aag aag aag     302
Phe Glu Ile Lys Pro Asp Lys Met Ile Cys A la Asp Pro Lys Lys Lys
    65                  70                  75 tgg gtt cag gat gcc aag aag tac ctg gac c aa ata tcc caa act aca     350
Trp Val Gln Asp Ala Lys Lys Tyr Leu Asp G ln Ile Ser Gln Thr Thr
80                  85                  90 aag ccg taatcatcgt gcttgagatg acaaaccaga aaattgcttg a tttatttt       406
Lys Pro
 95 ccttcctaaa atgcattctg aaataatatt attattcccc aaagggatga c ttttattta    466 ataattttaa aaagcaaatt gcatttaagt tatcagtctt taaacatatc t tttatgtat    526 atcactcatt tttaaaggtt gccttgctct ctgtgaactc ccatccggta c cctgccatg    586
```

-continued

```
tgtaggaaat gtgactccag gcttgctgga gactctttct cctacctccc t ggactcttg    646 taaggatcca acaaagacca ttgatgtgaa attgcctttt aattttcaga g gacattgtt    706 cttgtgaagc caggttgtga ttcacagtga tgagtggaag taaatgtgtt t tcagaatac    766 atgaaatata tacatacttt attactgcta aaaaaaaaaa aaaaaaaaa a a             818
```

```
<210> SEQ ID NO 16
<211> LENGTH: 96
<212> TYPE: PRT
<213> ORGANISM: Guinea pig

<400> SEQUENCE: 16
```

Met Lys Val Ser Thr Ala Phe Leu Cys Leu L eu Leu Thr Val Ser Ala
1               5                   10                  15

Phe Ser Ala Gln Val Leu Ala His Pro Gly I le Pro Ser Ala Cys Cys
            20                  25                  30

Phe Arg Val Thr Asn Lys Lys Ile Ser Phe G ln Arg Leu Lys Ser Tyr
        35                  40                  45

Lys Ile Ile Thr Ser Ser Lys Cys Pro Gln T hr Ala Ile Val Phe Glu
    50                  55                  60

Ile Lys Pro Asp Lys Met Ile Cys Ala Asp P ro Lys Lys Trp Val
65                  70                  75                  80

Gln Asp Ala Lys Lys Tyr Leu Asp Gln Ile S er Gln Thr Thr Lys Pro
                85                  90                  95

```
<210> SEQ ID NO 17
<211> LENGTH: 151
<212> TYPE: DNA
<213> ORGANISM: Homo sapiens
<220> FEATURE:
<221> NAME/KEY: CDS
<222> LOCATION: (76)...(150)

<400> SEQUENCE: 17
```
cgagcggccg cccgggcgag gtcaacccag aaaccaccac ctctcacgcc a aagctcaca    60 ccttcagcct ccaac atg aag gtc tcc gca gca ctt ctg tgg ctg ctg ctc    111
                Met Lys Val Ser Ala Ala Leu Leu Trp Leu Leu Leu
                1               5                   10 ata gca gct gcc ttc agc ccc cag ggg ctc g ct ggg cca g                151
Ile Ala Ala Ala Phe Ser Pro Gln Gly Leu A la Gly Pro
            15                  20                  25

```
<210> SEQ ID NO 18
<211> LENGTH: 25
<212> TYPE: PRT
<213> ORGANISM: Homo sapiens

<400> SEQUENCE: 18
```

Met Lys Val Ser Ala Ala Leu Leu Trp Leu L eu Leu Ile Ala Ala Ala
1               5                   10                  15

Phe Ser Pro Gln Gly Leu Ala Gly Pro
            20                  25

```
<210> SEQ ID NO 19
<211> LENGTH: 153
<212> TYPE: DNA
<213> ORGANISM: Homo sapiens
<220> FEATURE:
<221> NAME/KEY: CDS
<222> LOCATION: (40)...(150)

<400> SEQUENCE: 19
```

-continued

```
tttttttttct ctctgttcat ttttttttccc caaaattca gct tct gt c cca acc      54
                                            Ala Ser Val Pro Thr
                                              1               5 acc tgc tgc ttt aac ctg gcc aat agg aag a ta ccc ctt cag cga cta     102
Thr Cys Cys Phe Asn Leu Ala Asn Arg Lys I le Pro Leu Gln Arg Leu
         10                      15                     20 gag agc tac agg aga atc acc agt ggc aaa t gt ccc cag aaa gct gtg     150
Glu Ser Tyr Arg Arg Ile Thr Ser Gly Lys C ys Pro Gln Lys Ala Val
             25                      30                   35 atg                                                                  153
```

<210> SEQ ID NO 20
<211> LENGTH: 37
<212> TYPE: PRT
<213> ORGANISM: Homo sapiens

<400> SEQUENCE: 20

Ala Ser Val Pro Thr Thr Cys Cys Phe Asn L eu Ala Asn Arg Lys Ile
 1               5                  10                      15

Pro Leu Gln Arg Leu Glu Ser Tyr Arg Arg I le Thr Ser Gly Lys Cys
             20                  25                      30

Pro Gln Lys Ala Val
         35

<210> SEQ ID NO 21
<211> LENGTH: 353
<212> TYPE: DNA
<213> ORGANISM: Homo sapiens
<220> FEATURE:
<221> NAME/KEY: CDS
<222> LOCATION: (13)...(114)

<400> SEQUENCE: 21

```
atctcccaca gc ttc aag acc aaa ctg gcc aag ga t atc tgt gcc gac ccc     51
               Phe Lys T hr Lys Leu Ala Lys Asp Ile Cys Ala Asp Pr o
                 1               5                  10 aag aag aag tgg gtg cag gat tcc atg aag t at ctg gac caa aaa tct      99
Lys Lys Lys Trp Val Gln Asp Ser Met Lys T yr Leu Asp Gln Lys Ser
 15                  20                      25 cca act cca aag cca taaataatca ccatttttga aaccaaac ca gagcctgagt     154
Pro Thr Pro Lys Pro
 30 gttgcctaat ttgttttccc ttcttacaat gcattctgag gtaacctcat t atcagtcca   214 aagggcatgg gttttattat atatatatat atttttttttt ttaaaaaaaa a cgtattgca  274 tttaatttat tgaggcttta aaacttatga tcctccatga atatcagtta t ttttaaact   334 gtaaagctat cgataccgt                                                 353
```

<210> SEQ ID NO 22
<211> LENGTH: 34
<212> TYPE: PRT
<213> ORGANISM: Homo sapiens

<400> SEQUENCE: 22

Phe Lys Thr Lys Leu Ala Lys Asp Ile Cys A la Asp Pro Lys Lys Lys
 1               5                  10                      15

Trp Val Gln Asp Ser Met Lys Tyr Leu Asp G ln Lys Ser Pro Thr Pro
             20                  25                      30

Lys Pro

```
<210> SEQ ID NO 23
<211> LENGTH: 70
<212> TYPE: PRT
<213> ORGANISM: Guinea pig

<400> SEQUENCE: 23

Ile Pro Ser Ala Cys Cys Phe Arg Val Thr A sn Lys Lys Ile Ser Phe
 1               5                   10                  15

Gln Arg Leu Lys Ser Tyr Lys Ile Ile Thr S er Ser Lys Cys Pro Gln
            20                  25                  30

Thr Ala Ile Val Phe Glu Ile Lys Pro Asp L ys Met Ile Cys Ala Asp
        35                  40                  45

Pro Lys Lys Lys Trp Val Gln Asp Ala Lys L ys Tyr Leu Asp Gln Ile
    50                  55                  60

Ser Gln Thr Thr Lys Pro
65                   70

<210> SEQ ID NO 24
<211> LENGTH: 73
<212> TYPE: PRT
<213> ORGANISM: Mus musculus

<400> SEQUENCE: 24

His Pro Gly Ser Ile Pro Thr Ser Cys Cys P he Ile Met Thr Ser Lys
 1               5                   10                  15

Lys Ile Pro Asn Thr Leu Leu Lys Ser Tyr L ys Arg Ile Thr Asn Asn
            20                  25                  30

Arg Cys Thr Leu Lys Ala Ile Val Phe Lys T hr Arg Gly Lys Glu Ile
        35                  40                  45

Cys Ala Asp Pro Lys Lys Lys Trp Val Gln A sp Ala Thr Lys His Leu
    50                  55                  60

Asp Gln Lys Leu Gln Thr Pro Lys Pro
65                  70

<210> SEQ ID NO 25
<211> LENGTH: 74
<212> TYPE: PRT
<213> ORGANISM: Homo sapiens

<400> SEQUENCE: 25

Gly Pro Ala Ser Val Pro Thr Thr Cys Cys P he Asn Leu Ala Asn Arg
 1               5                   10                  15

Lys Ile Pro Leu Gln Arg Leu Glu Ser Tyr A rg Arg Ile Thr Ser Gly
            20                  25                  30

Lys Cys Pro Gln Lys Ala Val Ile Phe Lys T hr Lys Leu Ala Lys Asp
        35                  40                  45

Ile Cys Ala Asp Pro Lys Lys Lys Trp Val G ln Asp Ser Met Lys Tyr
    50                  55                  60

Leu Asp Gln Lys Ser Pro Thr Pro Lys Pro
65                  70

<210> SEQ ID NO 26
<211> LENGTH: 605
<212> TYPE: DNA
<213> ORGANISM: Mus musculus

<400> SEQUENCE: 26
cgagcggccg cccgggcgag gtcaacccag aaaccaccac ctctcacgcc a aagctcaca     60
```

-continued

```
ccttcagcct caacatgaa ggtctccgca gcacttctgt ggctgctgct c atagcagct    120 gccttcagcc cccaggggct cgctgggcca gcttctgtcc caaccacctg c tgctttaac    180 ctggccaata ggaagatacc ccttcagcga ctagagagct acaggagaat c accagtggc    240 aaatgtcccc agaaagctgt gatcttcaag accaaactgg ccaaggatat c tgtgccgac    300 cccaagaaga agtgggtgca ggattccatg aagtatctgg accaaaaatc t ccaactcca    360 aagccataaa taatcaccat ttttgaaacc aaaccagagc ctgagtgttg c ctaatttgt    420 tttcccttct tacaatgcat tctgaggtaa cctcattatc agtccaaagg g catgggttt    480 tattatatat atatatattt tttttttttaa aaaaaaacgt attgcattta a tttattgag    540 gctttaaaac ttatgatcct ccatgaatat cagttatttt taaactgtaa a gctatcgat    600 accgt                                                                605
```

<210> SEQ ID NO 27
<211> LENGTH: 97
<212> TYPE: PRT
<213> ORGANISM: Homo sapiens

<400> SEQUENCE: 27

Met Lys Val Ser Ala Ala Leu Leu Trp Leu Leu Leu Ile Ala Ala Ala
1               5                   10                  15

Phe Ser Pro Gln Gly Leu Ala Gly Pro Ala Ser Val Pro Thr Thr Cys
                20                  25                  30

Cys Phe Asn Leu Ala Asn Arg Lys Ile Pro Leu Gln Arg Leu Glu Ser
            35                  40                  45

Tyr Arg Arg Ile Thr Ser Gly Lys Cys Pro Gln Lys Ala Val Ile Phe
        50                  55                  60

Lys Thr Lys Leu Ala Lys Asp Ile Cys Ala Asp Pro Lys Lys Lys Trp
65                  70                  75                  80

Val Gln Asp Ser Met Lys Tyr Leu Asp Gln Lys Ser Pro Thr Pro Lys
                85                  90                  95

Pro